(12) United States Patent
Ridder et al.

(10) Patent No.: US 7,403,804 B2
(45) Date of Patent: Jul. 22, 2008

(54) NONINVASIVE DETERMINATION OF ALCOHOL IN TISSUE

(75) Inventors: Trent D. Ridder, Sandia Park, NM (US); John D. Maynard, Albuquerque, NM (US); Russell E. Abbink, Sandia Park, NM (US); Robert D. Johnson, Albuquerque, NM (US); Edward L. Hull, Fairport, NY (US); Andrew D. Meigs, Albuquerque, NM (US); Alan Ross, Albuquerque, NM (US); Dashiell A. Birnkrant, Albuquerque, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 222 days.

(21) Appl. No.: 10/852,415

(22) Filed: May 24, 2004

(65) Prior Publication Data
US 2005/0261560 A1      Nov. 24, 2005

Related U.S. Application Data

(63) Continuation-in-part of application No. 10/281,576, filed on Oct. 28, 2002, now Pat. No. 7,202,091, which is a continuation-in-part of application No. 09/832,608, filed on Apr. 11, 2001, now Pat. No. 6,983,176, application No. 10/852,415, which is a continuation-in-part of application No. 10/378,237, filed on Mar. 3, 2003, now Pat. No. 6,865,408, which is a continuation-in-part of application No. 09/832,585, filed on Apr. 11, 2001, now Pat. No. 6,574,490, and a continuation-in-part of application No. 10/281,576, filed on Oct. 28, 2002, now Pat. No. 7,202,091, application No. 10/852,415, which is a continuation-in-part of application No. 10/753,506, filed on Jan. 8, 2004, now Pat. No. 7,016,713.

(51) Int. Cl.
*A61B 5/1455* (2006.01)

(52) U.S. Cl. .................................................. 600/310
(58) Field of Classification Search ................. 600/309, 600/310, 314, 322, 323, 326, 473
See application file for complete search history.

(56) References Cited

U.S. PATENT DOCUMENTS 4,898,172 A * 2/1990 Grable ........................ 600/249

(Continued)

OTHER PUBLICATIONS

James W. Brault, *New Approach to High-Precision Fourier Transform Spectrometer Design*, Applied Optics, vol. 35, No. 16, Jun. 1, 1996, pp. 2891-2896.

(Continued)

*Primary Examiner*—Eric F Winakur
(74) *Attorney, Agent, or Firm*—V. Gerald Grafe

(57) ABSTRACT

An apparatus and method for non-invasive determination of attributes of human tissue by quantitative infrared spectroscopy. The system includes subsystems optimized to contend with the complexities of the tissue spectrum, high signal-to-noise ratio and photometric accuracy requirements, tissue sampling errors, calibration maintenance problems, and calibration transfer problems. The subsystems include an illumination subsystem, a tissue sampling subsystem, a spectrometer subsystem, a data acquisition subsystem, and a processing subsystem. The invention is applicable, as examples, to determining the concentration or change of concentration of alcohol in human tissue.

28 Claims, 27 Drawing Sheets

U.S. PATENT DOCUMENTS

| | | | |
|---|---|---|---|
| 4,975,581 A | 12/1990 | Robinson et al. | 250/339 |
| 5,435,309 A * | 7/1995 | Thomas et al. | 600/310 |
| 5,615,673 A * | 4/1997 | Berger et al. | 600/326 |
| 5,830,132 A | 11/1998 | Robinson | 600/310 |
| 5,914,780 A | 6/1999 | Turner et al. | 356/346 |
| 6,016,435 A * | 1/2000 | Maruo et al. | 600/316 |
| 6,157,041 A | 12/2000 | Thomas et al. | 250/573 |
| 6,219,565 B1 * | 4/2001 | Cupp et al. | 600/310 |
| 6,678,541 B1 * | 1/2004 | Durkin et al. | 600/310 |
| 6,687,521 B2 * | 2/2004 | Sato et al. | 600/344 |
| 2003/0023152 A1 * | 1/2003 | Abbink et al. | 600/316 |
| 2005/0002031 A1 * | 1/2005 | Kraemer et al. | 356/337 |
| 2005/0135766 A1 * | 6/2005 | Cianciotto et al. | 385/133 |

OTHER PUBLICATIONS

John C. Brasunas and G. Mark Cusman, *Uniform Time-Sampling Fourier Transform Spectroscopy*, Applied Optics, vol. 36, No. 10, Apr. 1, 1997, pp. 2206-2210.

* cited by examiner

NONINVASIVE DETERMINATION OF ALCOHOL IN TISSUE

CROSS REFERENCES TO CO-PENDING APPLICATIONS

This application
(a) is a continuation-in-part of U.S. patent application Ser. No. 10/281,576, entitled "Optically Similar Reference Samples", filed Oct. 28, 2002, now U.S. Pat. No. 7,202,091 issued Apr. 10, 2007, incorporated herein by reference, which is a continuation-in-part of U.S. patent application Ser. No. 09/832,608, entitled "Optically Similar Reference Samples and Related Methods for Multivariate Calibration Models Used in Optical Spectroscopy," filed Apr. 11, 2001, now U.S. Pat. No. 6,983,176 issued Jan. 3. 2006; and
(b) is a continuation-in-part of U.S. patent application Ser. No. 10/378,237, entitled "System For Non-Invasive Measurement Of Glucose In Humans," filed Mar. 3, 2003, now U.S. Pat. No. 6,865,408 issued Mar. 8, 2005, incorporated herein by reference, which is
   (b1) a continuation-in-part of U.S. patent application Ser. No. 09/832,585, entitled "System For Non-Invasive Measurement Of Glucose In Humans." filed Apr. 11, 2001, now U.S. Pat. No. 6,574,490 issued Jun. 3, 2003, incorporated herein by reference; and
   (b2) a continuation-in-part of U.S. patent application Ser. No. 10/281,576, entitled "Optically Similar Reference Samples", filed Oct. 28, 2002, now U.S. Pat. No. 7,202, 091 issued Apr. 10, 2007; and
(c) is a continuation-in-part of U.S. patent application Ser. No. 10/753,506, "Noninvasive Determination of Direction and Rate of Change of an Analyte," filed Jan. 8, 2004, now U.S. Pat. No. 7,016,713 issued Mar. 21, 2006, incorporated herein by reference.

FIELD OF THE INVENTION

The present invention generally relates to the use of spectroscopy for measuring alcohol presence or concentration utilizing non-invasive techniques in combination with multivariate analysis.

BACKGROUND OF THE INVENTION

Current practice for alcohol measurements is based upon either blood measurements or breath testing. Blood measurements are generally considered the most accurate for determining alcohol intoxication levels. However, blood measurements require a venous or capillary sample and involve significant handling precautions in order to minimize health risks. Once extracted, the blood sample must be properly labeled and transported to a clinical laboratory or other suitable location. A clinical gas chromatograph is typically used to measure the alcohol level in the sample. Due to the invasiveness of the procedure and the amount of sample handling involved, blood alcohol measurements are usually limited to critical situations such as for traffic accidents, violations where the suspect requests this type of test, and accidents where injuries are involved.

Because it is less invasive, breath testing is more commonly encountered in the field. In breath testing, the subject must expire air into the instrument for a sufficient time and volume to achieve a stable breath flow that originates from the alveoli deep within the lungs. The device then measures the alcohol content in the air, which is related to blood alcohol through a breath-blood partition coefficient. The blood-breath partition coefficient used in the United States is 2100 (implied units of mg EtOH/dL blood per mg EtOH/dL air) and varies between 1900 and 2400 in other nations. The partition coefficient is highly subject dependent. In other words, each subject will have a partition coefficient in the 1900 to 2400 range, depending on his or her physiology. Since knowledge of each subject's partition coefficient is unavailable in field applications, each nation assumes a single partition coefficient value that is globally applied to all measurements. In the U.S., defendants in DUI cases often use the globally applied partition coefficient as an argument to impede prosecution.

Breath measurements have additional limitations. First, the presence of "mouth alcohol" can falsely elevate the breath alcohol measurement. This necessitates a 15-minute waiting period prior to making a measurement in order to ensure that no mouth alcohol is present. For a similar reason, a 15 minute delay is required for individuals who are observed to burp or vomit. A delay of 10 minutes or more can be required between breath measurements to allow the instrument to return to equilibrium with the ambient air and zero alcohol levels. In addition, the accuracy of breath alcohol measurements is sensitive to numerous physiological and environmental factors.

Multiple government agencies, and society in general, seek non-invasive alternatives to blood and breath alcohol measurements. Quantitative spectroscopy offers the potential for a completely non-invasive alcohol measurement that is not sensitive to the limitations of the current measurement methodologies. While non-invasive determination of biological attributes by quantitative spectroscopy has been found to be highly desirable, it has been very difficult to accomplish. Attributes of interest include, as examples, analyte presence, analyte concentration (e.g., alcohol concentration), direction of change of an analyte concentration, rate of change of an analyte concentration, disease presence (e.g., alcoholism), disease state, and combinations and subsets thereof. Non-invasive measurements via quantitative spectroscopy are desirable because they are painless, do not require a fluid draw from the body, carry little risk of contamination or infection, do not generate any hazardous waste, and can have short measurement times.

Several systems have been proposed for the non-invasive determination of attributes of biological tissue. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photo-acoustic spectroscopy, and near-infrared spectroscopy. However, these systems have not replaced direct and invasive alcohol measurements.

As an example, Robinson et al. in U.S. Pat. No. 4,975,581 disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as alcohol, but also can be any chemical or physical property of the sample. The method of Robinson et al. involves a two-step process that includes both calibration and prediction steps.

In the calibration step, the infrared light is coupled to calibration samples of known characteristic values so that there is attenuation of at least several wavelengths of the infrared radiation as a function of the various components and analytes comprising the sample with known characteristic value. The infrared light is coupled to the sample by passing the light through the sample or by reflecting the light off the sample. Absorption of the infrared light by the sample causes intensity variations of the light that are a function of the wavelength of the light. The resulting intensity variations at a minimum of several wavelengths are measured for the set of calibration samples of known characteristic values. Original or transformed intensity variations are then empirically related to the known characteristics of the calibration samples using multivariate algorithms to obtain a multivariate calibration model. The model preferably accounts for subject variability, instrument variability and environment variability.

In the prediction step, the infrared light is coupled to a sample of unknown characteristic value, and a multivariate calibration model is applied to the original or transformed intensity variations of the appropriate wavelengths of light measured from this unknown sample. The result of the prediction step is the estimated value of the characteristic of the unknown sample. The disclosure of Robinson et al., U.S. Pat. No. 4,975,581, is incorporated herein by reference.

A further method of building a calibration model and using such model for prediction of analytes and/or attributes of tissue is disclosed in commonly assigned U.S. Pat. No. 6,157,041 to Thomas et al., entitled "Method and Apparatus for Tailoring Spectrographic Calibration Models," the disclosure of which is incorporated herein by reference.

In U.S. Pat. No. 5,830,132, Robinson describes a general method of robust sampling of tissue for non-invasive analyte measurement. The sampling method utilizes a tissue-sampling accessory that is pathlength optimized by spectral region for measuring an analyte such as alcohol. The patent discloses several types of spectrometers for measuring the spectrum of the tissue from 400 to 2500 nm, including acousto-optical tunable filters, discrete wavelength spectrometers, filters, grating spectrometers and FTIR spectrometers. The disclosure of Robinson, U.S. Pat. No. 5,830,132, is incorporated herein by reference.

In "New Approach to High-Precision Fourier Transform Spectrometer Design", Applied Optics, 35:16, 2891-2895, 1996, Brault introduces a constant time sampling analog-to-digital conversion technique for FTIR spectrometers that allows use of high dynamic range delta-sigma ADCs. Brault asserts their approach provides a superior technique for implementing the data acquisition system of an FTIR spectrometer because it avoids the artifacts of gain ranging and the need to precisely match the time delays between the laser reference and infrared measurement channels. In "Uniform Time-Sampling Fourier Transform Spectroscopy", Applied Optics, 36:1-, 2206-2210, 1997, Brasunas et al. discuss a variation of Brault's constant time sampling analog-to-digital conversion technique for FTIR spectrometers.

In U.S. Pat. No. 5,914,780, Turner et al. describe a method of digitizing the interferogram of an FTIR spectrometer using a constant time sampling analog-to-digital converter. The constant time sampling technique allows the use of high dynamic range, delta-sigma analog-to-digital converters that obviate the need for gain ranging circuitry and precisely matched delays between the reference laser and infrared signals. This type of data acquisition system is asserted to provide the FTIR spectrometer with higher SNR and superior photometric accuracy when compared to the previously employed sampling technique which is triggered by the zero crossings of the reference laser.

Although there has been substantial work conducted in attempting to produce commercially viable non-invasive near-infrared spectroscopy-based systems for determination of biological attributes, no such device is presently available.

It is believed that prior art systems discussed above have failed for one or more reasons to fully meet the challenges imposed by the spectral characteristics of tissue which make the design of a non-invasive measurement system a formidable task. Thus, there is a substantial need for a commercially viable device that can provide sufficient accuracy and precision.

SUMMARY OF THE INVENTION

The present invention is directed to methods and apparatuses for the non-invasive determination of the presence or concentration of analytes such as alcohol in human tissue by infrared spectroscopy.

The present system overcomes the challenges posed by the spectral characteristics of tissue by incorporating an optimized design characterized, for discussion purposes, as six subsystems. The design contends with the complexities of the tissue spectrum, high signal-to-noise ratio and photometric accuracy requirements, tissue sampling errors, calibration maintenance problems, calibration transfer problems plus a host of other issues. The six subsystems include an illumination subsystem, a tissue sampling subsystem, an spectrometer subsystem, a data acquisition subsystem, a computing subsystem, and a calibration subsystem. Note that in some embodiments functions of the subsystems can be combined or separated into fewer or more subsystems; the separation into six is for convenience of description only.

The present invention further includes apparatuses and methods that allow for implementation and integration of each of these subsystems in order to optimize the net attribute signal-to-noise ratio in view of the desired performance, cost, size, and other characteristics of the system. The net attribute signal is the portion of the near-infrared spectrum that is specific for the attribute of interest because it is orthogonal to all other sources of spectral variance. The orthogonal nature of the net attribute signal makes it perpendicular to the space defined by any interfering species and as a result, the net attribute signal is uncorrelated to these sources of variance. The net attribute signal-to-noise ratio is directly related to the accuracy and precision of the present invention for non-invasive determination of the attribute by quantitative near-infrared spectroscopy.

The present invention can use near-infrared radiation for analysis. Radiation in the wavelength range of 1.2 to 2.5 microns (a frequency range of 8000 to 4000 $cm^{-1}$) can be suitable for making some non-invasive measurements because such radiation has acceptable specificity for a number of analytes, including alcohol, along with tissue optical penetration depths of up to 5 millimeters with acceptable absorbance characteristics. In the 1.2 to 2.5 micron spectral region, the large number of optically active substances that make up the tissue complicate the measurement of any given substance due to the overlapped nature of their absorbance spectra. Multivariate analysis techniques can be used to resolve these overlapped spectra such that accurate measurements of the substance of interest can be achieved. Multivariate analysis techniques, however, can require that multivariate calibrations remain robust over time (calibration maintenance) and be applicable to multiple instruments (calibration transfer).

The present invention documents a multidisciplinary approach to the design of a spectroscopic instrument that incorporates an understanding of the instrument subsystems, tissue physiology, multivariate analysis, near-infrared spectroscopy and overall system operation. Further, the interactions between the subsystems have been analyzed so that the behavior and requirements for the entire non-invasive measurement device are well understood and result in a design for a commercial instrument that will make non-invasive measurements with sufficient accuracy and precision at a price and size that is commercially viable.

The subsystems of the non-invasive monitor are highly optimized to provide reproducible and, preferably, uniform radiance of the tissue, low tissue sampling error, depth targeting of the tissue layers that contain the property of interest, efficient collection of diffuse reflectance spectra from the tissue, high optical throughput, high photometric accuracy, large dynamic range, excellent thermal stability, effective calibration maintenance, effective calibration transfer, built-in quality control, and ease-of-use.

DETAILED DESCRIPTION OF THE INVENTION

The following detailed description should be read with reference to the drawings. The drawings, which are not necessarily to scale, depict illustrative embodiments that are not intended to limit the scope of the invention.

For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure. The term "alcohol" is used as an example analyte of interest; the term is intended to include any one or combination of ethanol, methanol, ethyl glycol, and any chemical commonly referred to as alcohol.

Figure 1:
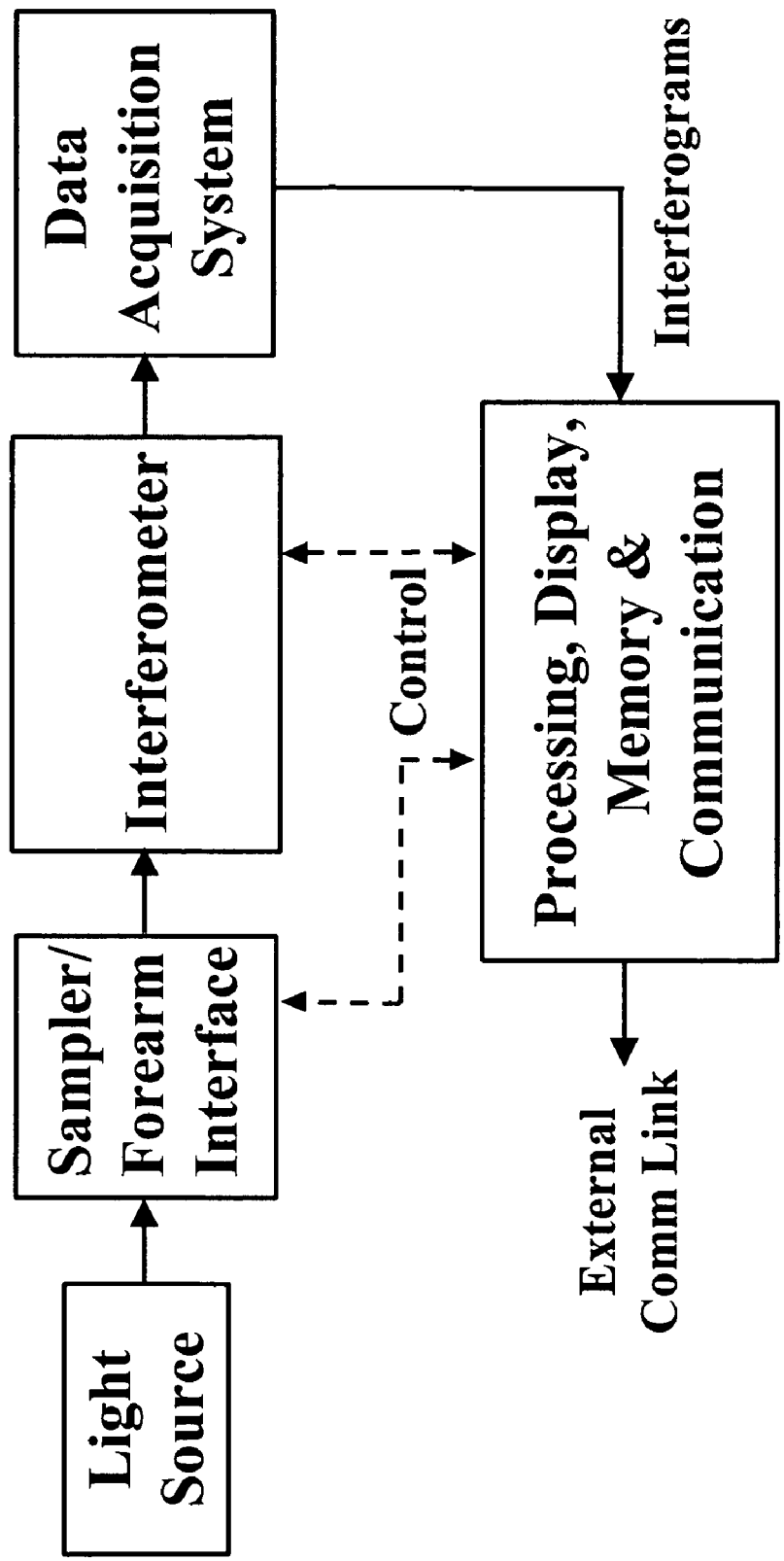
FIG. 1 is a schematic depiction of a non-invasive spectrometer system according to the present invention.
Figure 2:
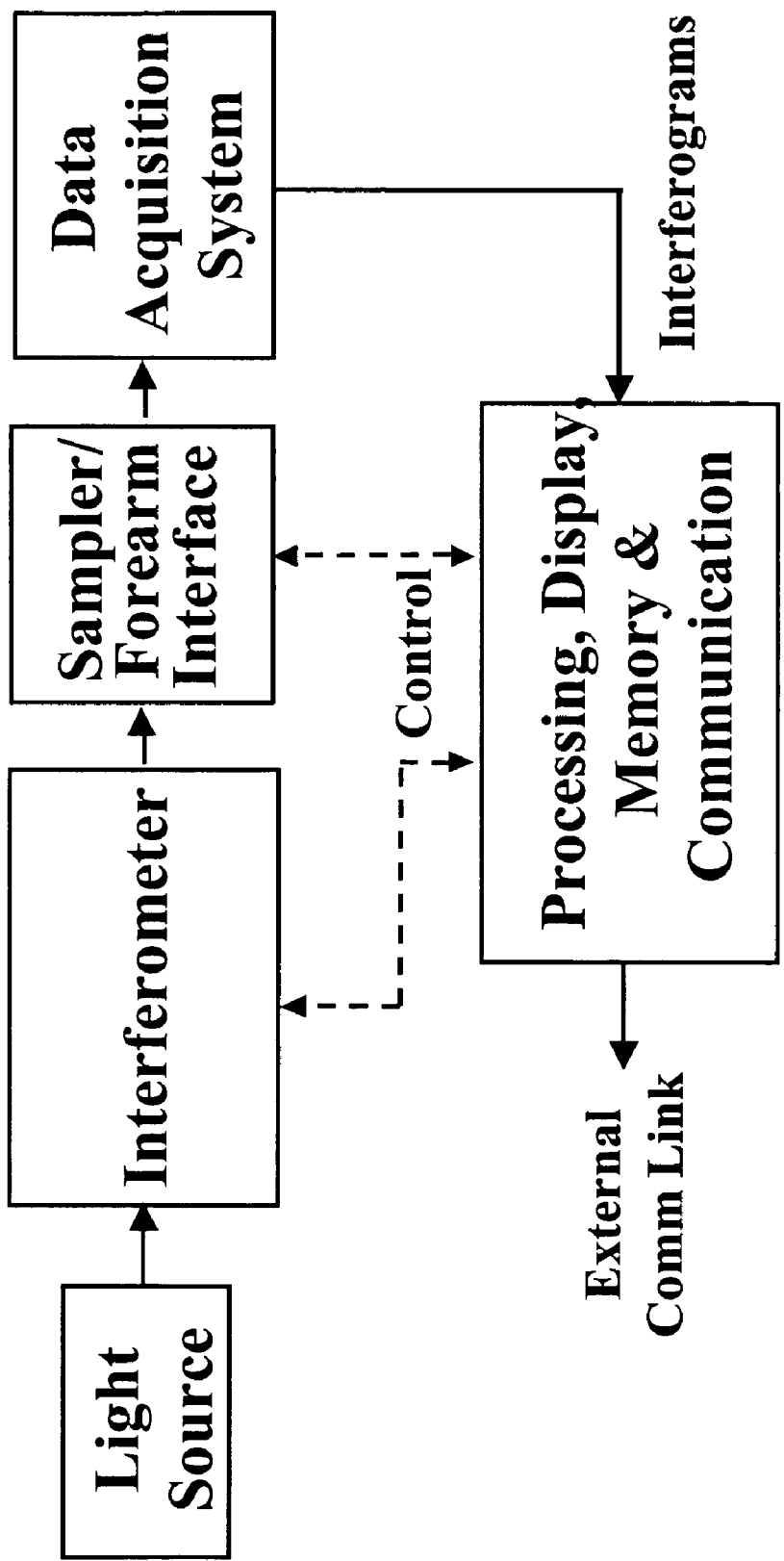
FIG. 2 is a schematic depiction of a non-invasive spectrometer system according to the present invention.

FIG. 1 is a schematic depiction of a non-invasive monitor. The overall system can be viewed for discussion purposes as comprising six subsystems; those skilled in the art will appreciate other subdivisions of the functionality disclosed. The subsystems include an illumination subsystem (Light Source), a tissue sampling subsystem (Sampler/Forearm Interface), a spectrometer subsystem (Interferometer), a data acquisition subsystem, a processing subsystem (Processing, Display, Memory, and Communication), which includes a calibration subsystem. The subsystems can be designed and integrated in order to achieve a desirable net attribute signal-to-noise ratio. FIG. 2 is a schematic depiction of an alternative arrangement of the elements shown in FIG. 1: the interferometer and sampler/forearm interface have been exchanged relative to the monitor of FIG. 1. Those skilled in the art will appreciate the effect of interchanging elements in an optical path; subsequent discussion assumes the arrangement of FIG. 1 for simplicity, but is not meant to preclude alternative arrangements of the subsystems.

Figure 3:
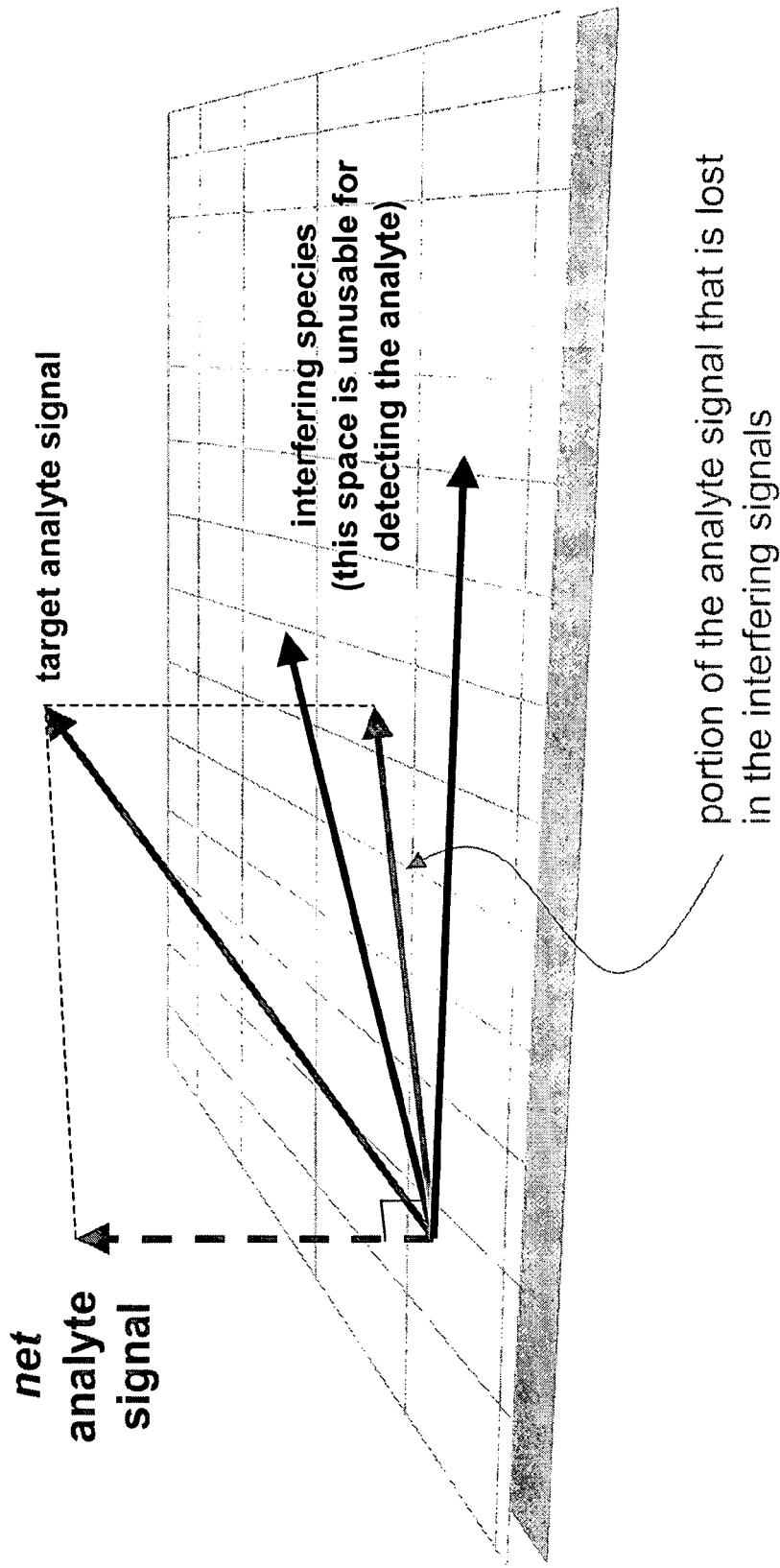
FIG. 3 is a graphical depiction of the concept of net attribute signal in a three-component system.

FIG. 3 is a graphical representation of the net attribute signal in a three dimensional system. The net attribute signal-to-noise ratio is directly related to the accuracy and precision of the non-invasive attribute determination by quantitative near-infrared spectroscopy with the present invention.

The subsystems provide reproducible and preferably uniform radiance of the tissue, low tissue sampling error, depth targeting of appropriate layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of the subsystems is discussed below in detail.

Illumination Subsystem

The illumination subsystem generates near-infrared (NIR) light used to interrogate the tissue. The illumination subsystem, in some embodiments, contains a broadband, polychromatic light source that emits radiation in the NIR portion of the spectrum. In the example illumination subsystem shown in FIG. 4, the light source can also emit radiation outside of the NIR. An example of a suitable light source is a 40-watt, 22.8-volt tungsten filament lamp. The light source can be driven by a tightly regulated power supply. The power supply can supply the lamp with constant current, constant voltage, or constant power. The power supply for the light source can provide regulation of current, voltage, or power in order to keep the color temperature and emissivity of the light source as stable as possible. Fluctuations of the light source's color temperature and emissivity can be a source of noise in the measurement and can reduce the net attribute signal and, subsequently, the accuracy and precision of the measurement.

Figure 4:
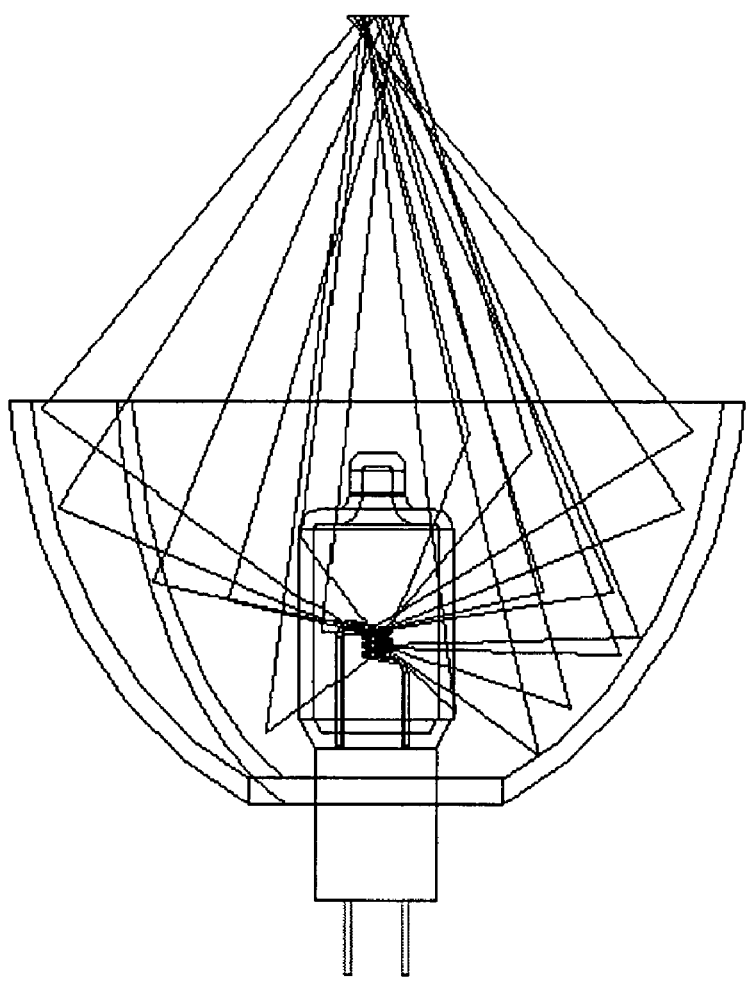
FIG. 4 is a diagrammed view of an example embodiment of a tungsten filament light source.

In some embodiments, the overall system of the present invention includes a power supply that provides regulated, low noise power to all of the subsystems. The power supply can be a 300-watt, quad output, resonant power, medical grade, AC power to DC converter that provides output voltages of +28, +15, −15, and +5 VDC. The ripple on each of the voltages can be less than 20 millivolts peak-to-peak and the switching frequency of the supply can be greater than 200 kilohertz to facilitate additional filtering of the power and to further reduce noise. Additionally, the power supply can have a conversion efficiency of at least 80%, which can be important to reduce the thermal loading of the non-invasive monitor so that only convection cooling is required for normal device operation. The illumination subsystem 100 can utilize the 28 VDC power from the power supply to drive the light source. A DC-to-DC converter can regulate the input power to 21.4 VDC and also can provide a soft start function that gradually turns on the light source when the monitor is first turned on. The soft start function can extend the useful life of the light source by eliminating startup transients and limiting the current required to initially power the light source. FIG. 4 is a diagramed view of an embodiment of a tungsten filament lamp.

Figure 5:
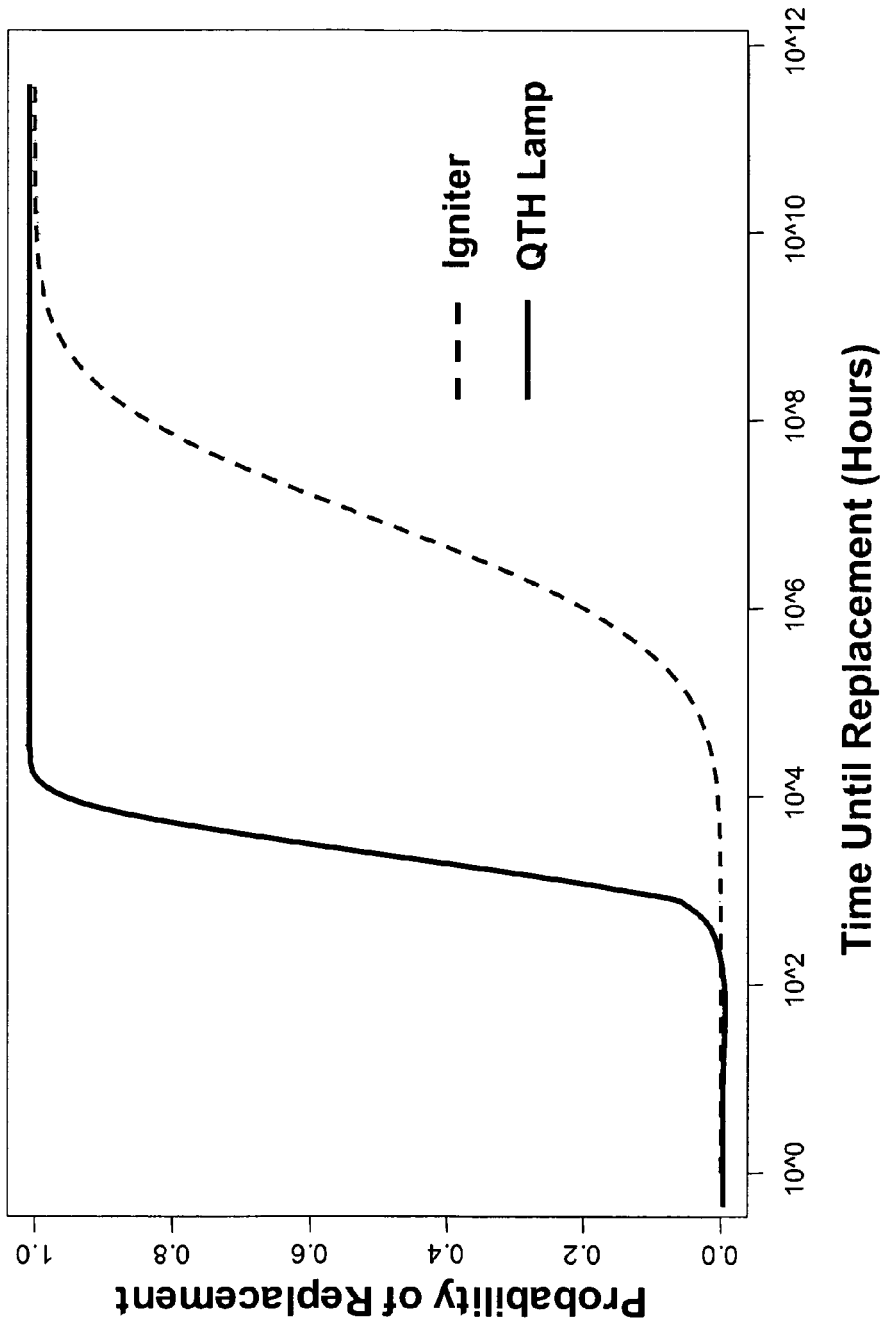
FIG. 5 shows the results of a long-term reliability study for igniter based light sources.

Another example light source is a resistive element such as those commonly used as igniters for furnaces and stoves. These light sources have a lower color temperature than standard filament lamps and are therefore more efficient in the near-infrared spectral region. These sources also have comparatively large emissive surfaces that are less sensitive to spatial effects that are encountered throughout the lifetime of the light source. An additional advantage of igniter-based light sources is a substantially longer lifetime when compared to filament lamps. FIG. 5 shows the results from a long-term study of over 50 igniters. The results of the study indicate that the expected lifetime of an igniter light source is 2 years (at a 10% failure rate) which is a significant improvement over filament light sources.

In addition to lifetime, igniter light sources offer a mechanical stability advantage as well as the potential to eliminate optical components, such as optical filters, that might otherwise be necessary: Filament based lamps such as QTH light sources can suffer from mechanical deformation of the filament over time. This mechanical deformation can result in complex changes in the angular and spatial distribution of the light being delivered to the tissue. Angular and spatial scramblers, such as light pipes and diffusers, can be used to mitigate these changes. However, the mechanical stability of igniter light sources can provide superior angular and spatial output stability and can allow for a much simpler and less expensive illumination system.

In QTH based embodiments; the light sources can require optical filters to reduce the amount of short wavelength light delivered to the tissue. This filtering keeps the total amount of infrared radiation being absorbed by the tissue from exceeding thermal damage threshold levels and also preferentially weights the spectral emission of the QTH more towards the 2 to 2.4 micron region for improved SNR performance. The lower color temperature of the igniter sources combined with a non-imaging illumination system, such as an integrating chamber, provides an illumination system with desirable spectral energy weighting without incurring the cost and complexity of additional optical filters.

Figure 6:
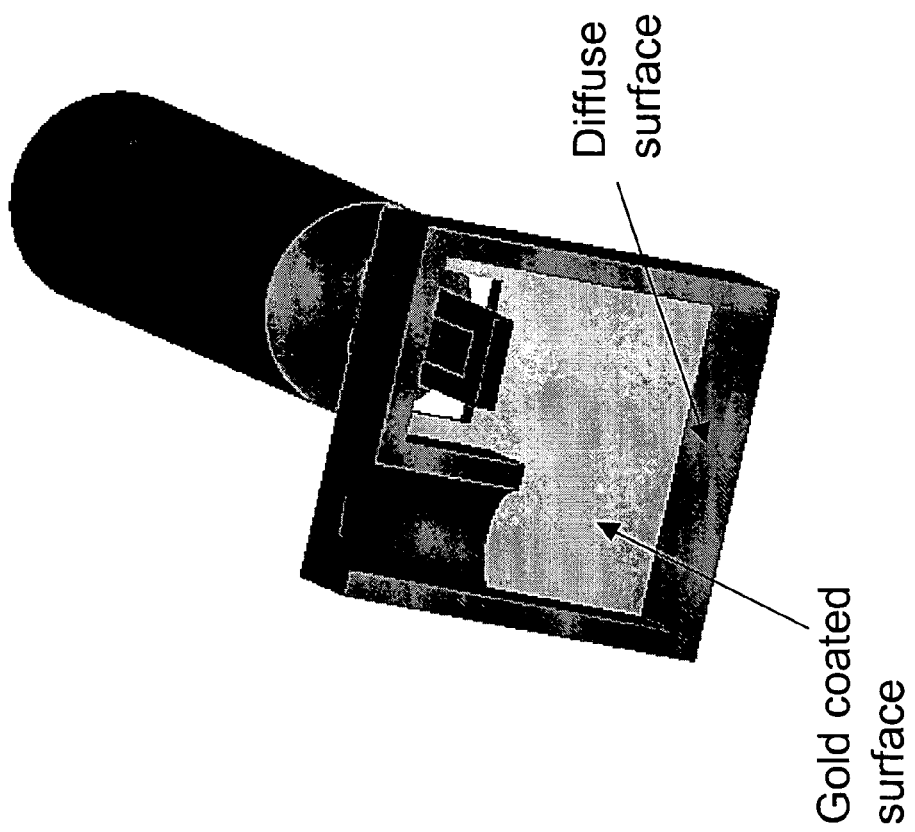
FIG. 6 is a diagrammed view of an example embodiment of an igniter light source in an integrating chamber.

In addition to the light source and regulated power supply, the illumination subsystem can contain optical elements that collect the radiation from the light source and transfer that light to the input of the tissue sampling subsystem. The elements that comprise the transfer optics can include collimating and/or condensing optics, optical filters, optical diffusers, a reflective integrating chamber, a diffuse integrating chamber, a homogenizer or light pipe for scrambling and the corresponding mechanical components to hold the optics and light source. FIG. 6 is a diagramed view of an embodiment of the illumination subsystem where an igniter light source is enclosed in an integrating chamber.

Figure 7:
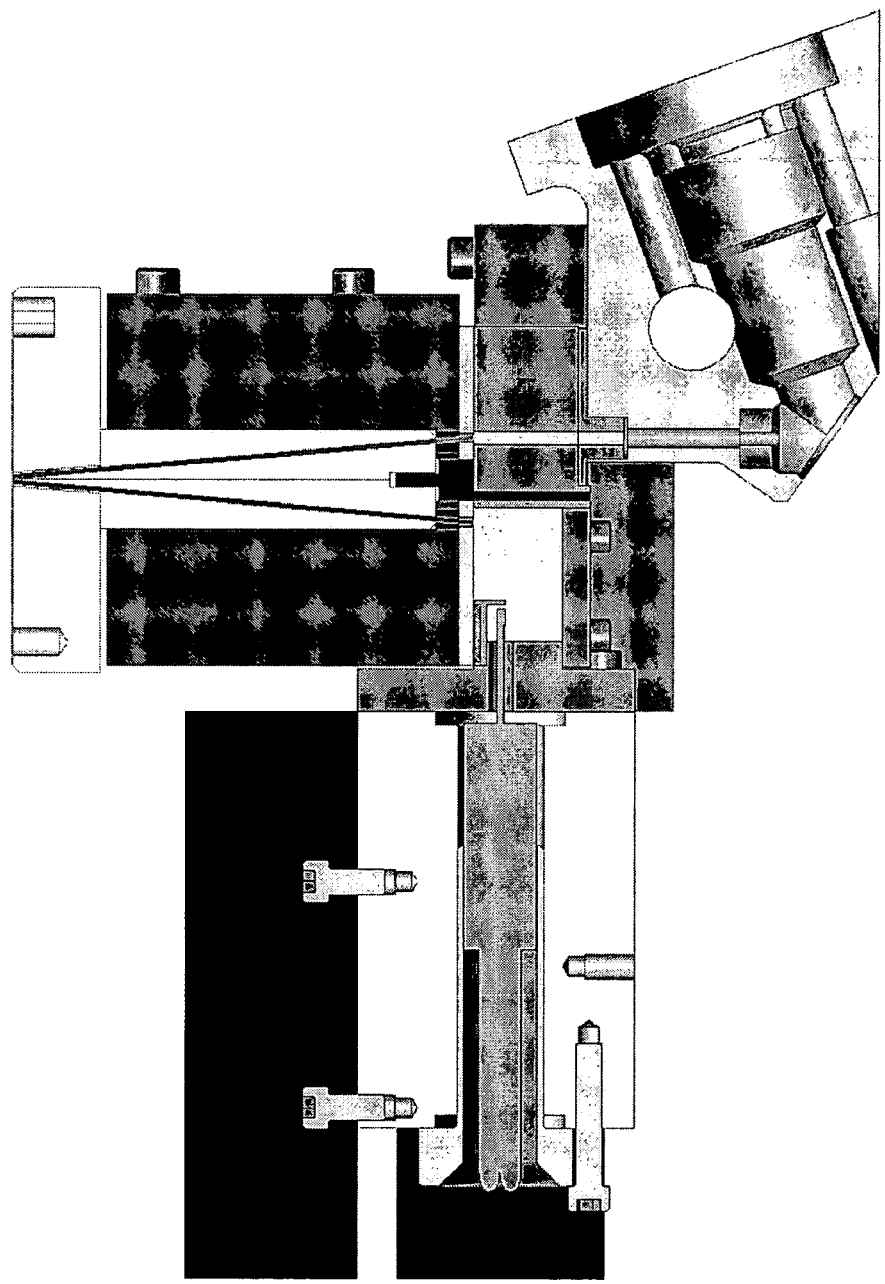
FIG. 7 is a diagrammed view of an example embodiment of a combined light source—tissue sampling subsystem.

In some embodiments, the illumination subsystem can also contain the optical elements that deliver light to the tissue. In these embodiments, the illumination subsystem can be considered a part of the tissue sampling subsystem. In this case, the number of overall optical components can be reduced which can result in a reduced cost, an improvement in optical efficiency, and smaller physical size. FIG. 7 is a graphical representation of a preferred embodiment where the illumination subsystem has been incorporated into the tissue sampling subsystem.

The collimating optics can be refractive or reflective elements. A lens is an example of a refractive collimating optic. A parabolic mirror is an example of a reflective collimating optic. The condensing optics can also be refractive or reflective. A lens is an example of a refractive condensing optic. An elliptical mirror is an example of a reflective condensing optic. Suitable materials for lenses and mirrors are known in the art. The reflective optics can have a smooth finish, a rough finish or a faceted finish depending on the configuration of the illumination subsystem. The rough or faceted finishes for the reflective optics destroy the coherence of the light source image to create a more uniform radiance pattern. The refractive optics can be spherical or aspherical. A Fresnel lens, a special type of aspherical lens, also can be employed. The collimating and/or condensing optics collect radiation from the source and transfer the radiation to the input of the tissue sampling subsystem or to other optical elements that perform additional operations on the light before it is passed to the tissue sampling subsystem.

One or more optical filters can be employed to preferentially pass radiation in the spectral region of interest. The optical filter can be one or a combination of long pass, short pass, or band pass filters. These filters can be absorptive, interference or dichroic in nature, as examples. The optical filters can be anti-reflection coated to preserve the transmittance of light in the spectral region of interest. These filters can also perform spectral shaping of the radiation from the light source to emphasize certain portions of the NIR spectrum over others. The optical filtering can bandlimit the radiation impinging on the tissue to increase the SNR in the region of interest and to keep from burning or otherwise damaging the tissue of the subject. Bandlimiting the radiation can improve the net attribute signal by reducing Shot noise that results from unwanted radiation outside the spectral region of interest.

Figure 8:
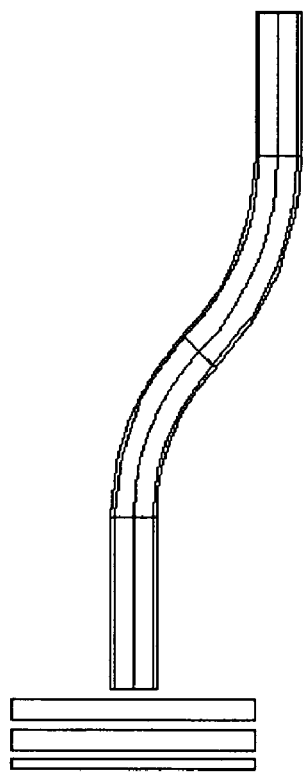
FIG. 8 is a diagramed view of a system of the present invention using a means for spatially and angularly homogenizing emitted radiation.
Figure 8:
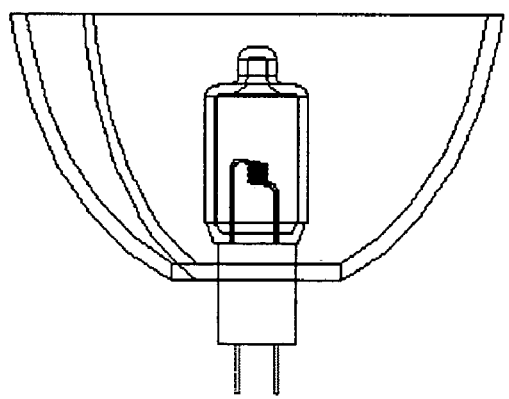

Optical diffusers and scramblers in the illumination subsystem provide reproducible and, preferably, uniform radiance at the input of the tissue sampling subsystem. Uniform radiance can ensure good photometric accuracy and even illumination of the tissue. Uniform radiance can also reduce errors associated with manufacturing differences between light sources. Uniform radiance can be utilized in the present invention for achieving accurate and precise measurements. FIG. 8 is a diagramed view of an embodiment of the illumination subsystem where a filament lamp is used in conjunction with an optical diffuser and scrambler in order to provide uniform radiance at the input of the sampling subsystem. See, e.g., U.S. Pat. No. 6,684,099, incorporated herein by reference.

A ground glass plate is an example of an optical diffuser. The ground surface of the plate effectively scrambles the angle of the radiation emanating from the light source and its transfer optics. A light pipe can be used to scramble the intensity of the radiation such that the intensity is spatially uniform at the output of the light pipe. In addition, light pipes with a double bend will scramble the angles of the radiation. Circular light pipe cross sections can discourage creation of uniform spatial intensity and angular distribution. Square, hexagonal and octagonal cross sections can be effective scrambling geometries. The output of the light pipe can directly couple to the input of the tissue sampler or can be used in conjunction with additional transfer optics before the light is sent to the tissue sampler. See, e.g., U.S. patent application Ser. No. 09/832,586, "Illumination Device and Method for Spectroscopic Analysis," incorporated herein by reference.

Sampling Subsystem

Figure 9:
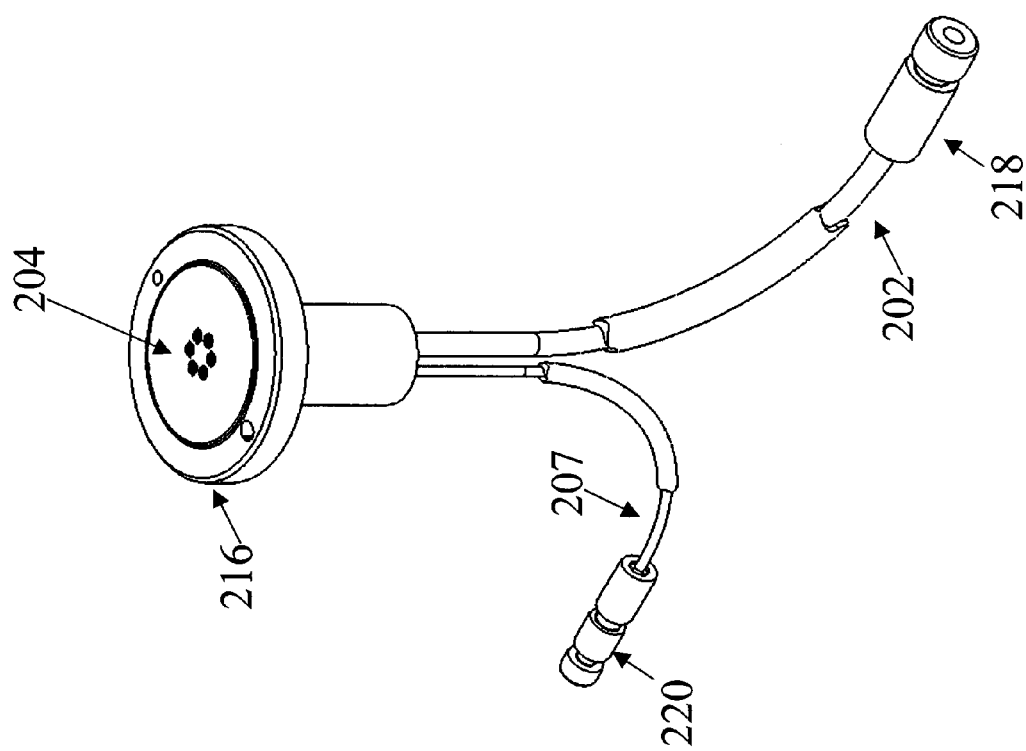
FIG. 9 is a perspective view of elements of an example tissue sampling subsystem.

As illustrated in FIG. 1, the tissue sampling subsystem introduces radiation generated by the illumination subsystem into the tissue of the subject, collects the portions of the radiation that are not absorbed by the tissue and sends that radiation to a spectrometer subsystem for measurement. FIGS. 9 through 17 depict elements of a preferred tissue sampling subsystem. Referring to FIG. 9, the tissue sampling subsystem has an optical input 202, a sampling surface 204 which forms a tissue interface that interrogates the tissue and an optical output 207. The subsystem can further include an ergonomic apparatus, depicted in FIG. 10, which holds the sampling surface 204 and positions the tissue at the interface. In a preferred subsystem, a device that thermostats the tissue interface is included and, in some embodiments, an apparatus that repositions the tissue on the tissue interface in a repetitive fashion is included. In other embodiments, an index matching fluid can be used to improve the optical interface between the tissue and sampling surface. The improved interface can reduce error and increase the efficiency, thereby improving the net attribute signal. See, e.g. U.S. Pat. No. 6,152,876 to Robinson et al., incorporated herein by reference.

Figure 11:
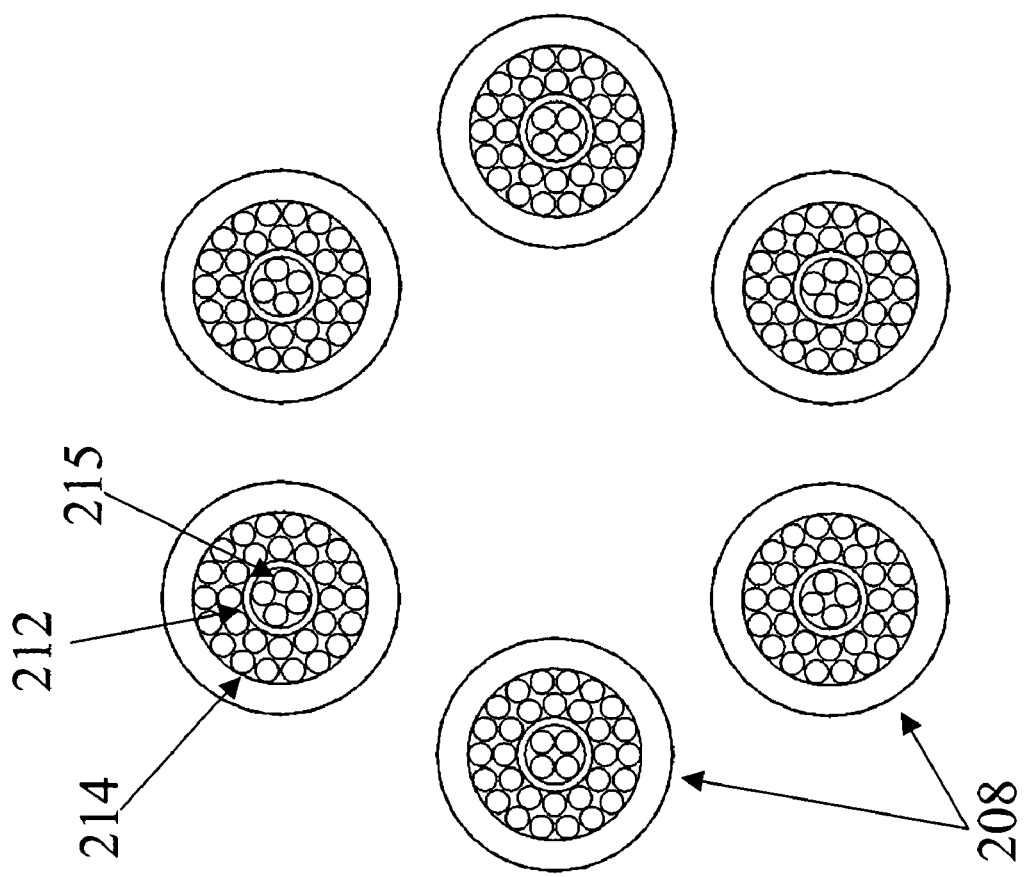
FIG. 11 is a plan view of the sampling surface of the tissue sampling subsystem, showing an example arrangement of input and output optical fiber ends.

The optical input 202 of the tissue sampling subsystem receives radiation from the illumination subsystem (e.g., light exiting a light pipe) and transfers that radiation to the tissue interface. As an example, the optical input can comprise a bundle of optical fibers that are arranged in a geometric pattern that collects an appropriate amount of light from the illumination subsystem. FIG. 11 depicts one example arrangement. The plan view depicts the ends of the input and output fibers in a geometry at the sampling surface including six clusters 208 arranged in a circular pattern. Each cluster includes four central output fibers 212, which collect diffusely reflected light from the tissue. Around each grouping of four central output fibers 212 is a cylinder of material 215, which ensures about a 100 µm gap between the edges of the central output fibers 212 and the inner ring of input fibers 214. The 100 µm gap can be important to measuring certain analytes. As shown in FIG. 11, two concentric rings of input fibers 214 can be arranged around the cylinder of material 215. As shown in one example embodiment, 32 input fibers surround four output fibers.

Figure 12:
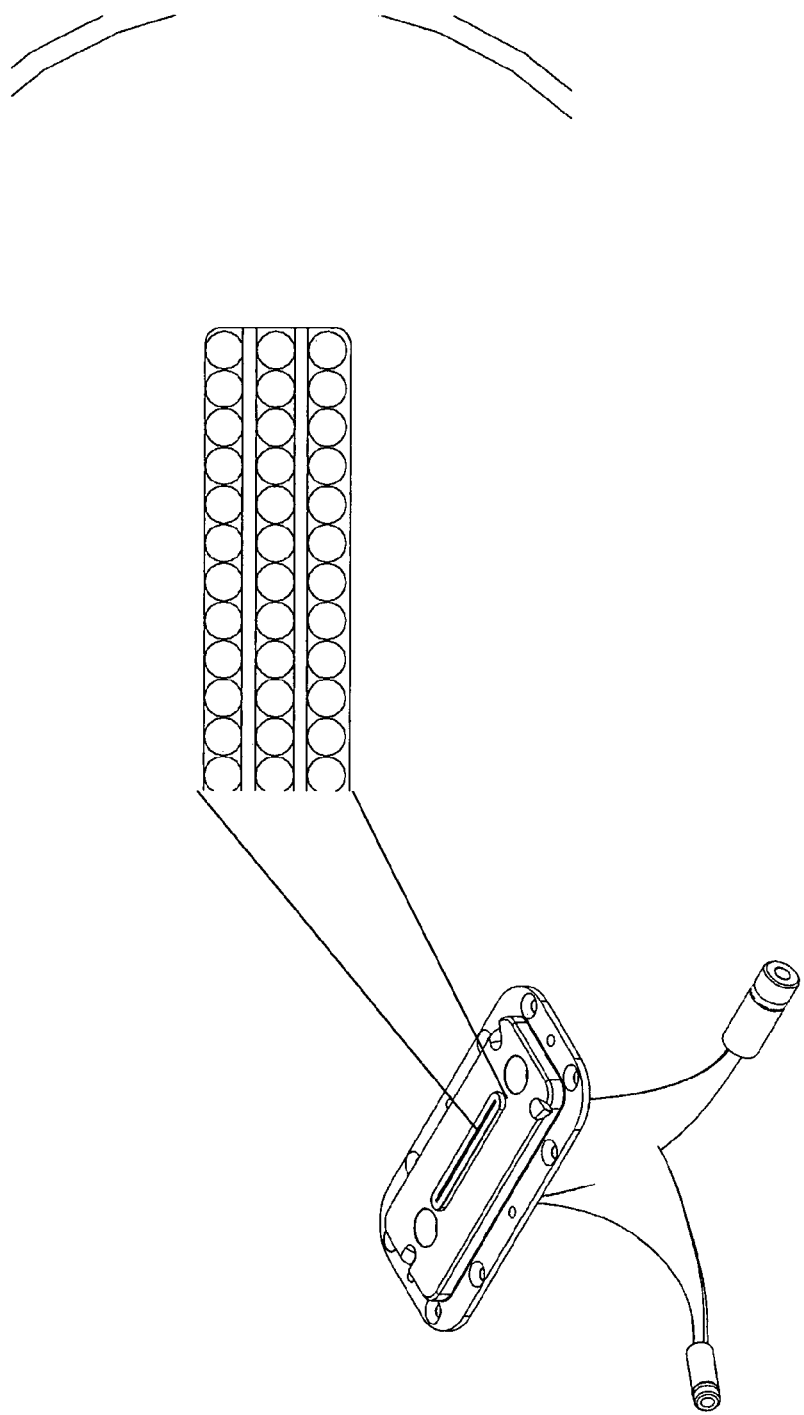
FIG. 12 is an alternative embodiment of the sampling surface of the tissue sampling subsystem.

FIG. 12 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to alter the physical area covered by the sampling subsystem. The total number of potential illumination fibers can depend on the physical size of emissive area of the light source and the diameter of each fiber. Multiple light sources can be used to increase the number of illumination fibers. The number of collection fibers can depend on the area of the interface to the interferometer subsystem. If the number of collection fibers results in an area larger than the interferometer subsystem interface allows, a light pipe or other homogenizer followed by an aperture can be used to reduce the size of the output area of the sampling subsystem. The light pipe or other homogenizer can encourage that each collection fiber contributes equally to the light that passes through the aperture.

Figure 13:
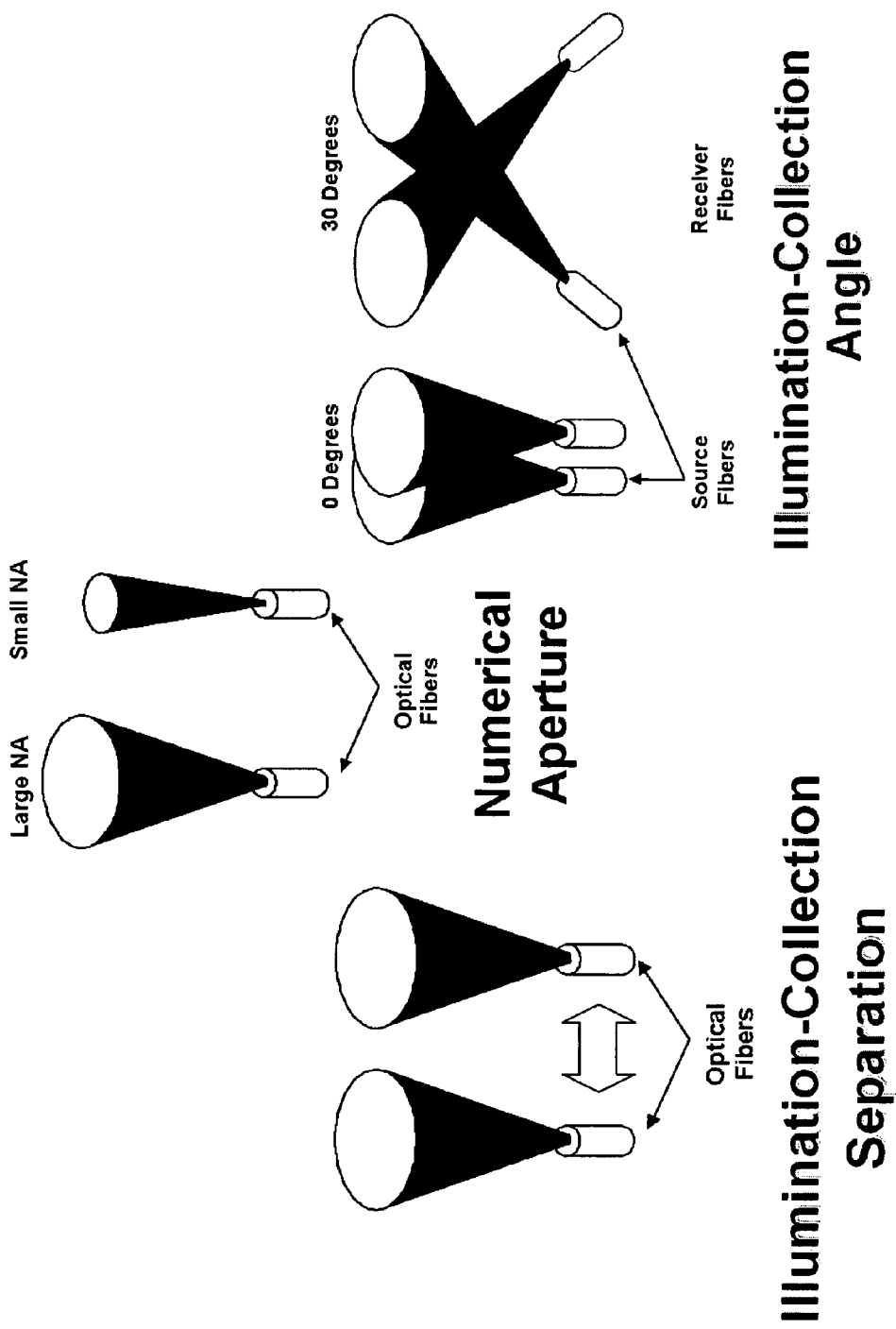
FIG. 13 is a depicts the various aspects of a sampler orientation.
Figure 14:
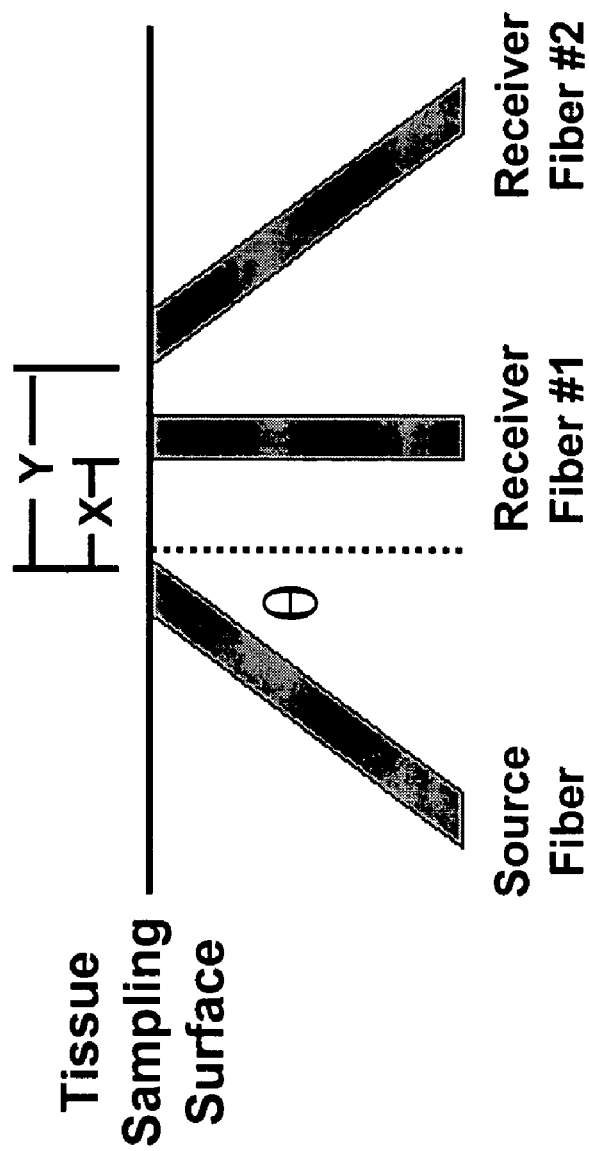
FIG. 14 is a diagramed view of a two-channel sampling subsystem.

The sampling subsystem can use one or more channels, where a channel refers to a specific orientation of the illumination and collection fibers. An orientation comprises the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 13 is a diagram of parameters that form an orientation. Multiple channels can be used in conjunction, either simultaneously or serially, to improve the accuracy of the noninvasive measurements. FIG. 14 is a diagram of a two channel sampling subsystem. In this example, the two channels are measuring the same tissue structure. Therefore each channel provides a measurement of the same tissue from a different perspective. The second perspective helps to provide additional spectroscopic information that helps to decouple the signals due to scattering and absorption. Referring to FIG. 14, the group of fibers (1 source, 1 receiver #1, and 1 receiver #2 in this example) can be replicated 1 to N times in order to increase the sampler area and improve optical efficiency. Each of the fibers can have a different numerical aperture and angle (θ). The distances between fibers, X and Y, determine the source receiver separation. Furthermore, an additional source channel can be added that creates a 4-channel sampling subsystem. As an example, the illumination fibers can be disposed at an angle between 20 degrees and 30 degrees from normal to the tissue surface, inclined toward the detection fibers, and the detection fibers can be disposed at an angle between 20 degrees and 30 degrees from normal to the tissue surface, inclined toward the illumination fibers, and each illumination fiber can be separated from the nearest detection fiber inclined toward the illumination fiber by at least 75 microns. Those skilled in the art will appreciate many variations contemplated by the present invention and illustrated by the examples discussed.

Figure 15:
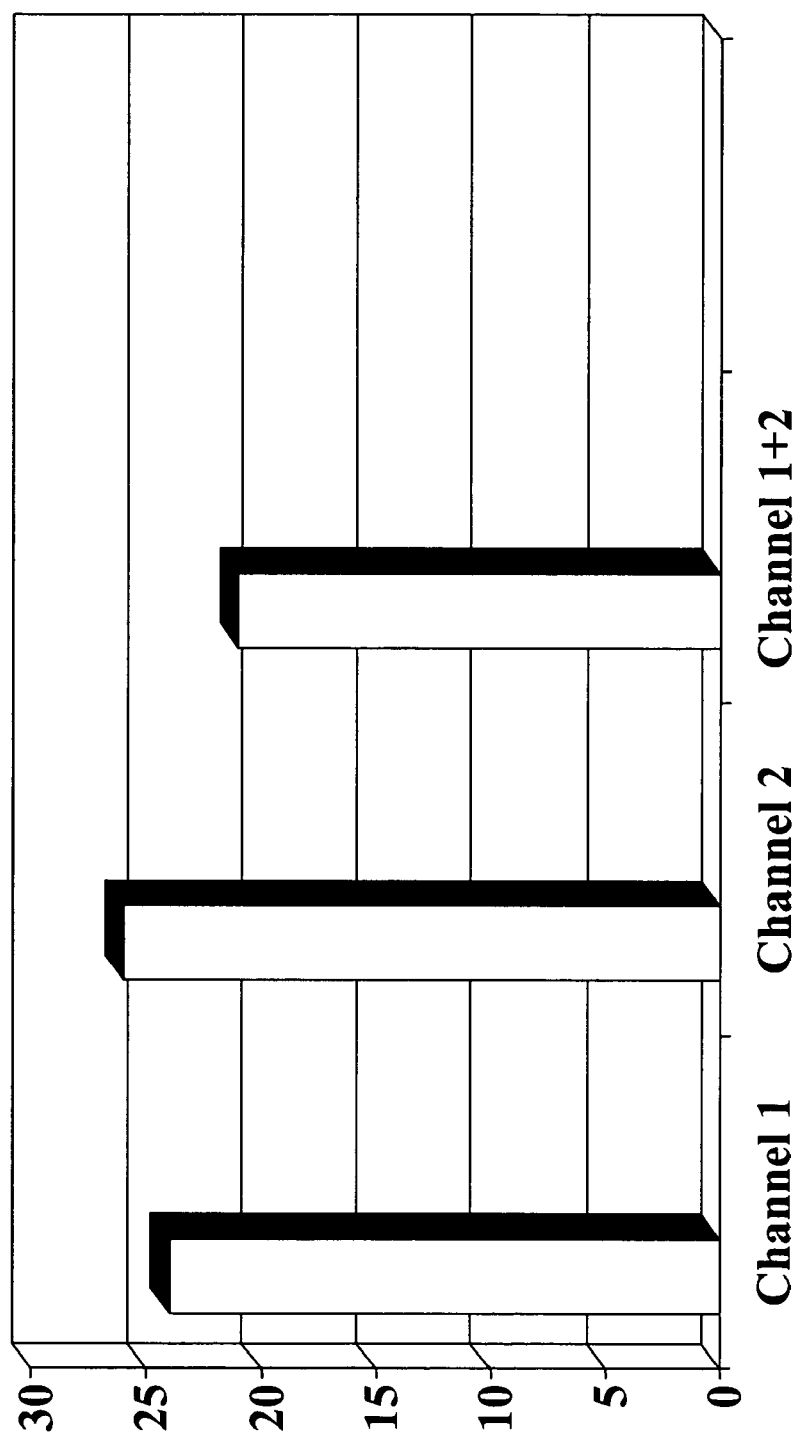
FIG. 15 is a graphical representation showing the benefits of a two-channel sampling subsystem.

FIG. 15 is a bar chart of example of the benefits of a multiple channel sampler that was used for noninvasive glucose measurements. The combination of the two channels provides superior measurement accuracy when compared to either channel individually. While this example uses two channels, additional channels can provide additional information that can further improve the measurement.

Figure 16:
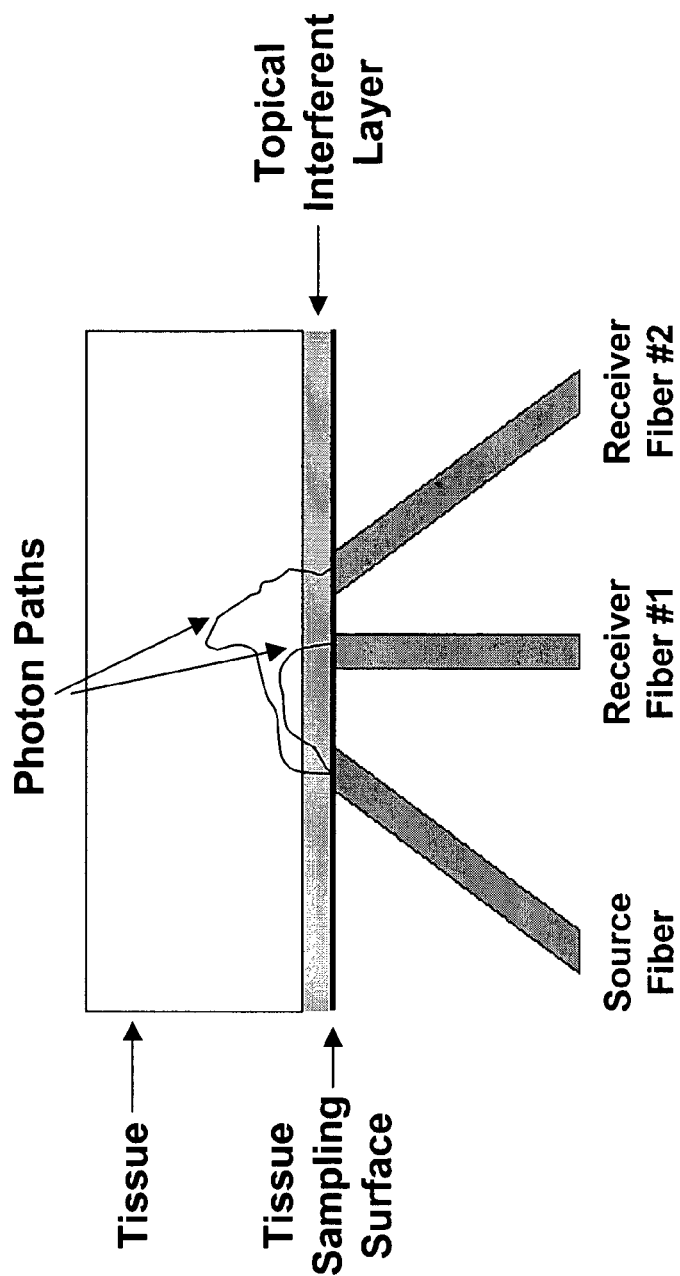
FIG. 16 is a diagramed view of the interface between the sampling surface and the tissue when topical interferants are present on the tissue.

Another aspect of a multiple channel sampling subsystem is the ability to improve detection and mitigation of topical interferants, such as sweat or lotion, present on the sample. FIG. 16 is a diagram of the multiple channel sampling subsystem in the presence of a topical interferant. The figure shows the sampling subsystem at the tissue interface, a layer of topical interferant, and the tissue. In this example the contribution to each channel's measurement due to the topical interferant is identical. This allows the potential to decouple the common topical interferant signal present in both channels from the tissue signal that will be different for the two channels.

The clustered input and output fibers can be mounted into a cluster ferrule that is mounted into a sampling head 216. The sampling head 216 includes a sampling surface 204, polished flat to encourage formation of a good tissue interface. Likewise, the input fibers can be clustered into a ferrule 218 connected at the input ends to interface with the illumination subsystem. The output ends of the output fibers can be clustered into a ferrule 220 for interface with the FTIR spectrometer subsystem.

Alternatively, the optical input can use a combination of light pipes, refractive and/or reflective optics to transfer input light to the tissue interface. The input optics of the tissue sampling subsystem should collect sufficient light from the illumination subsystem to achieve an acceptable net attribute signal. In one embodiment of the present invention, the placement of the illumination subsystem and tissue sampling subsystem before the spectrometer subsystem enhances throughput for a given size of spectrometer because the input to the tissue sampling subsystem is designed to handle the wide range of angles from the illumination subsystem and the small output image size of the tissue sampling subsystem is better matched to the throughput supported by a reasonably sized FTIR spectrometer.

The tissue interface can irradiate the tissue in a manner that targets the compartments of the tissue pertinent to the attribute of interest, and can discriminate against light that does not travel a significant distance through those compartments. As an example, a 100-μm gap discriminates against light that contains little attribute information. In addition, the tissue interface can average over a certain area of the tissue to reduce errors due to the heterogeneous nature of the tissue. The tissue sampling interface can reject specular and short pathlength rays and it can collect the portion of the light that travels the desired pathlength through the tissue with high efficiency to obtain a desirable net attribute signal. The tissue sampling interface can employ optical fibers to channel the light from the input to the tissue in a predetermined geometry as discussed above. The optical fibers can be arranged in patterns that target certain layers of the tissue that contain desired attribute information. The spacing, angle, numerical aperture, and placement of the input and output fibers can be arranged in a manner that achieves effective depth targeting. In addition to the use of optical fibers, the tissue sampling interface can use a non-fiber based arrangement that places a pattern of input and output areas on the surface of the tissue. Proper masking of the non-fiber based tissue sampling interface ensures that the input light travels a minimum distance in the tissue and contains valid attribute information. The tissue sampling interface can be thermostatted to control the temperature of the tissue in a predetermined fashion. The temperature of the tissue sampling interface can be controlled such that the invention reduces prediction errors due to temperature variation. Further, reference errors are reduced when building a calibration model. These methods are disclosed in commonly assigned U.S. patent application Ser. No. 09/343, 800, entitled "Method and Apparatus for Non-Invasive Blood Analyte Measurement with Fluid Compartment Equilibration," the disclosure of which is incorporated herein by reference.

Figure 10:
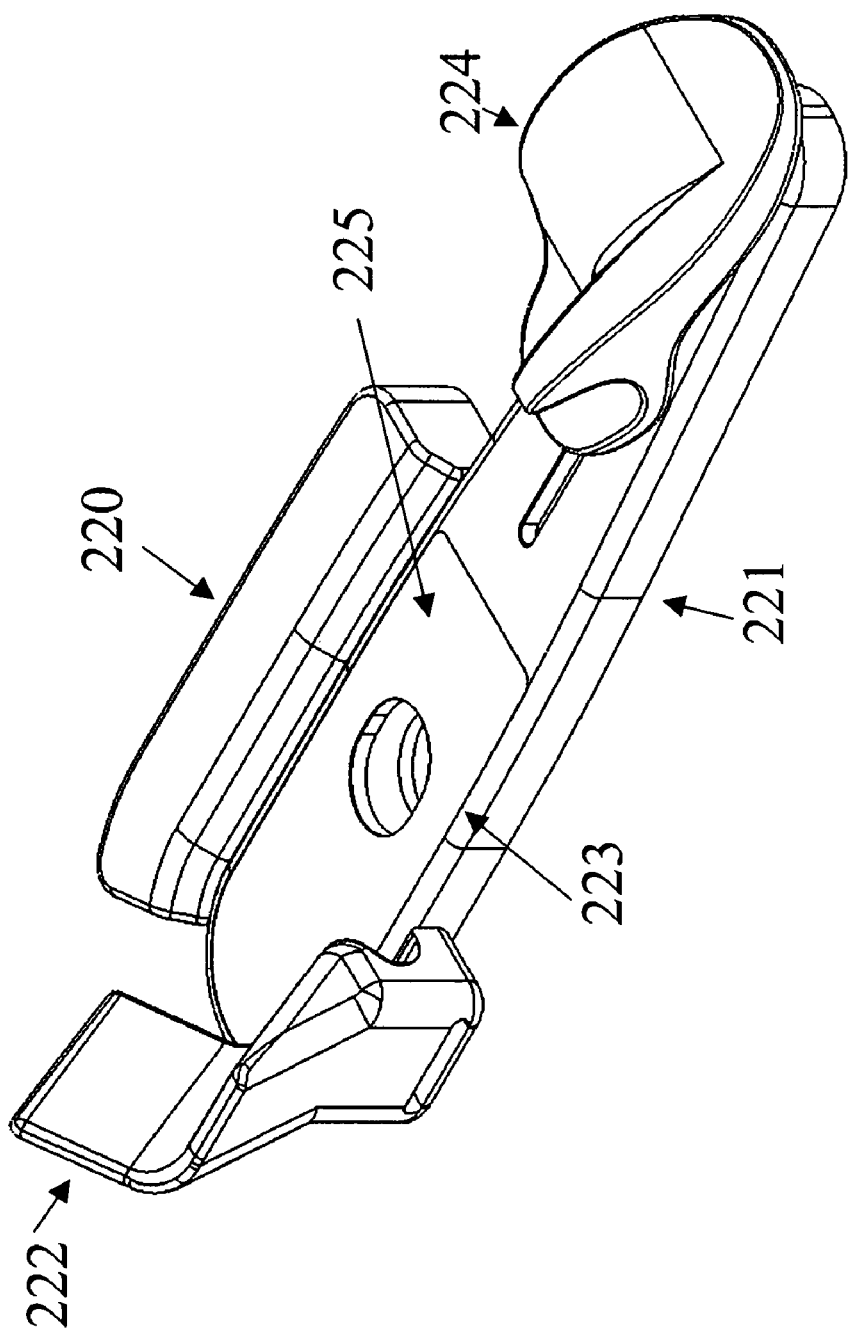
FIG. 10 is a perspective view of an ergonomic apparatus for holding the sampling surface and positioning a tissue surface thereon.

The tissue sampling subsystem can employ an ergonomic apparatus or cradle 210 that positions the tissue over the sampling interface in a reproducible manner. A preferred ergonomic apparatus is depicted in FIG. 10. In the case of sampling the underside of the forearm, an ergonomic cradle design can encourage good contact with the sampling interface. The ergonomic cradle includes a base 221 having an opening 223 therethrough. The opening receives the sample head 216 to position the sampling surface 204 generally coplanar with an upper surface 225 of the base 221. The ergonomic cradle references the elbow and upper arm of the subject via a bracket 222 in conjunction with a float-to-fit handgrip 224 to accurately position the forearm on the tissue sampling interface. Sampling error can result from improper sampling interface design.

The ergonomic cradle is designed such that the forearm of the subject is reliably located over the sampling head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position can be adjusted for each subject to accommodate different forearm lengths. In some embodiments, a lifting mechanism is included which raises and lowers the cradle periodically during sampling to break and reform the tissue interface. Reformation of the interface facilitates reduction of sampling errors due to the rough nature and heterogeneity of the skin. Alternate sites, for example fingertips, can also be accommodated using variations of the systems described herein.

Figure 17:
FIG. 17 is a diagramed view of an alternative positioning device for the tissue relative to the sampling surface.
Figure 17:
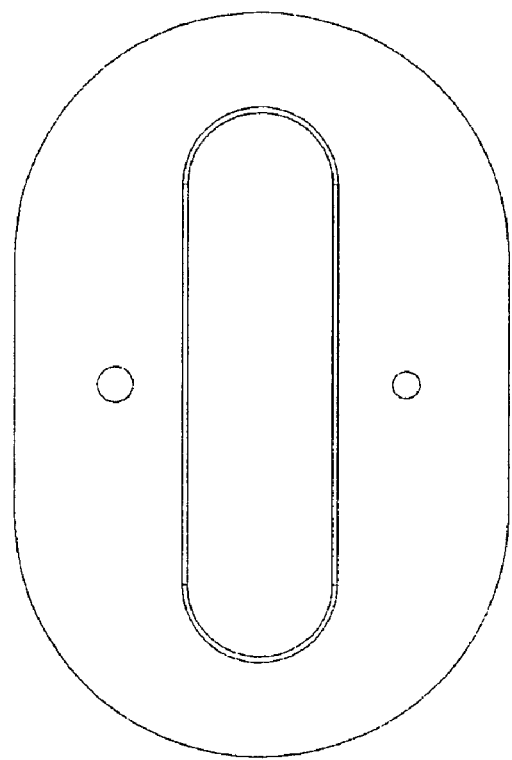

An alternative to the ergonomic cradle is diagrammed in FIG. 17. Instead of a cradle located on the measurement system, the positioning device is located on the tissue. The positioning device can either be reusable or disposable and can be adhered to the tissue with medical adhesive. The positioning device can also include an optically transparent film or other material that prevents physical contact with the sampling subsystem while preserving the desired optical characteristics of the measurement. The positioning device interfaces to the sampling subsystem in a pre-determined manner, such as alignment pins, in order to reproducibly locate the tissue to the sampling subsystem. The positioning device also prevents movement of the tissue relative to the sampling subsystem during the measurement process.

The image formed by the output of the tissue sampling subsystem is typically an order of magnitude smaller in size than its input. This input image to output image ratio can match the throughput supported by a spectrometer while maximizing the overall system signal to noise ratio. The output of the tissue sampling subsystem transfers the portion of the light not absorbed by the tissue that has traveled an acceptable path through the tissue to the input of the FTIR spectrometer subsystem. The output of the tissue sampling subsystem can use any combination of refractive and/or reflective optics to produce a collimated beam that can be modulated by a spectrometer. In some embodiments, the diffusely reflected light collected by the output fibers 207 of the sampler head 216 are collimated by a plano-aspheric lens made of ZnSe. The design of the lens is such that the collimated beam has less than five degrees of divergence. This lens is schematically depicted in FIG. 1 as part of the FTIR spectrometer subsystem. The collimating lens produces a beam with low optical distortion that serves as an input to the FTIR spectrometer discussed below.

Spectrometer Subsystem

Figure 18:
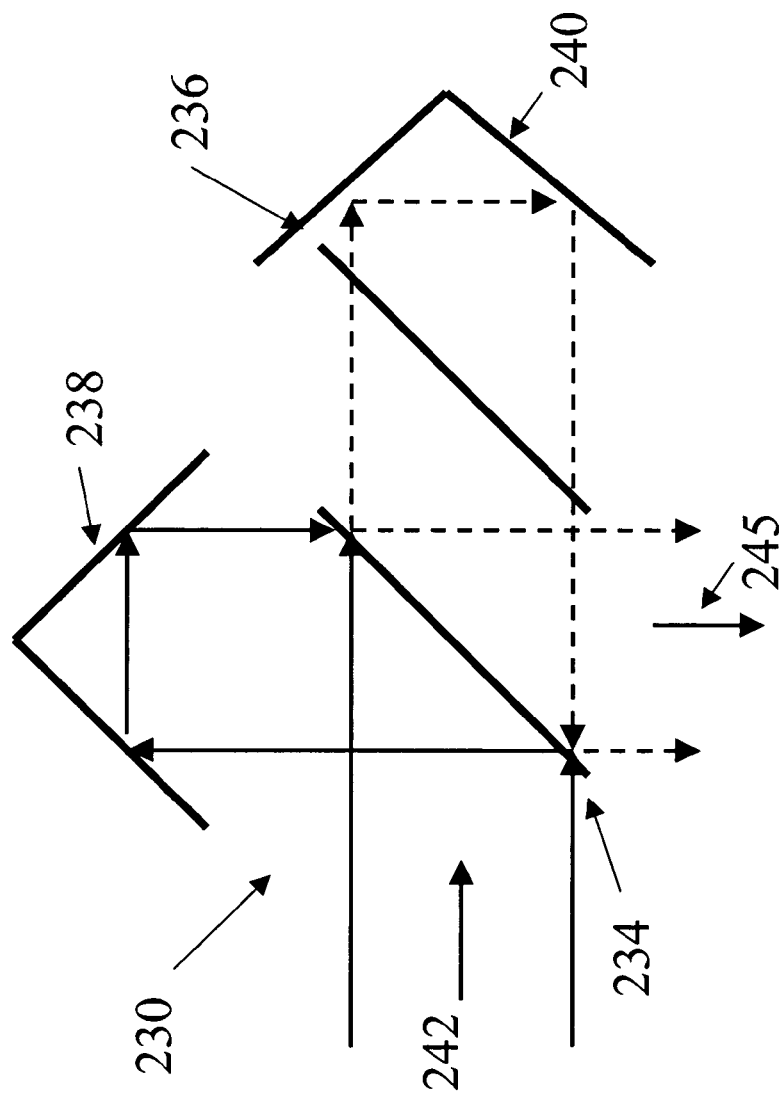
FIG. 18 is a simplified schematic view of an FTIR spectrometer utilized in a subsystem of the present invention.

As shown in FIG. 1, the spectrometer subsystem can include an FTIR or other type of spectrometer. The spectrometer spatially resolves or modulates different wavelengths of light such that their relative contribution to the overall signal can be determined. Dispersive spectrometers, such as those based on diffraction gratings, and interferometric spectrometers, such as Fourier transform infrared (FTIR) interferometers, are examples of suitable spectrometers. For convenience of discussion, an FTIR is used as an illustrative embodiment. The FTIR spectrometer modulates the sufficiently collimated light from the tissue sampling subsystem to create an interferogram that is received by the detector that is part of the data acquisition subsystem. The interferogram spatially encodes the NIR spectrum collected by the tissue sampling subsystem. FIG. 18 schematically depicts one embodiment of an FTIR spectrometer 230, which includes a beamsplitter 234 and compensator optics 236, a fixed retro-reflector 238 and a moving retro-reflector 240. The collimated input light 242 impinges on the beamsplitter optic 234 and is partially reflected and partially transmitted by the coating on the back surface of the beamsplitter 234. The reflected light passes back through the beamsplitter optic 234 and reflects off the fixed retro-reflector 238 and back to the beamsplitter 234. The transmitted light passes through the compensator optic 236 and reflects off the moving retro-reflector 240 and back to the beamsplitter 234. The transmitted and reflected portions of the light recombine at the beamsplitter to create an interference pattern or interferogram. The amount of constructive and/or destructive interference between the transmitted and reflected beams is dependent on the spectral content of the collimated input beam 242 and on the optical path difference between the fixed retro-reflector 238 and the moving retro-reflector 240. Other spectrometers can also be suitable. See, e.g., U.S. patent applications Ser. Nos. 10/342,578 and 10/614,267, each of which is incorporated herein by reference.

A reference laser can allow knowledge of the actual optical path difference as a function of time. Using the knowledge of the optical path difference, the infrared signal can be sampled in equal position increments to satisfy the requirements of a Fourier transform. A helium neon (HeNe) laser can be used as the reference in interferometers, and has been chosen in some applications because of its comparatively small size and cost relative to other gas lasers. A lower cost, solid state alternative to HeNe lasers is also suitable. See, e.g., U.S. Pat. No. 6,654,125, and U.S. application Ser. No. 10/678,843, each of which is incorporated herein by reference.

Figure 19:
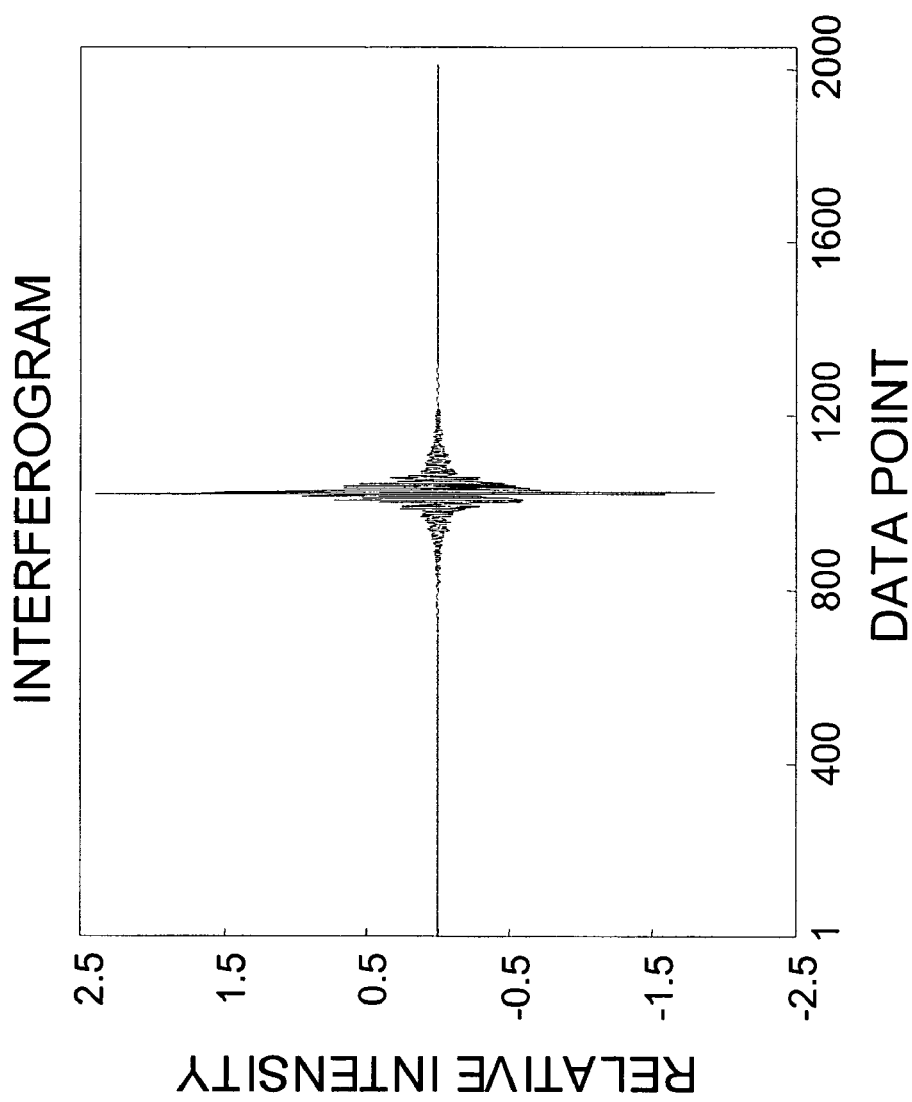
FIG. 19 depicts a typical interferogram created by the spectrometer of FIG. 18.

FIG. 19 shows a typical interferogram created by an FTIR spectrometer. At the point of zero path difference between the transmitted and reflected beams, there will be maximum constructive interference, and the centerburst of the interferogram is created. The interferogram is then focused onto a detector (part of the data acquisition subsystem), as shown in FIG. 1. The detector converts the optical interferogram into an electrical representation of the interferogram for subsequent digitizing by the data acquisition subsystem.

In an embodiment, the spectrometer subsystem utilizes an FTIR spectrometer 230 manufactured by Bomem. This spectrometer utilizes a single plate that contains beamsplitter and compensator functions. In addition, cube corners are used as the end mirrors and both cube corners are moved on a wishbone suspension to create the optical path difference and the subsequent interference record. The Bomem WorkIR™ FTIR spectrometer achieves thermal stability and spectral complexity performance useful for making non-invasive alcohol measurements with NIR spectroscopy. The FTIR spectrometer modulates the collimated light from the tissue sampler to spatially encode the NIR spectrum into an interferogram. Spectral resolution of the interferogram in the range of 2 to 64 wavenumbers can be suitable. Spectral resolution of 16-32 wavenumbers is suitable for many applications. The interferometer can produce either a single-sided or a double-sided interferogram, with the double-sided interferogram preferred in some applications because it achieves a higher net attribute signal and reduces sensitivity to phase errors. The resulting interferogram can be passed to a condensing lens, as shown in FIG. 1, and thereby focused onto the detector. The condensing lens can be a double convex design with each surface being asphencal in nature. In some embodiments, the lens material is ZnSe.

As an example application, the non-invasive measurement of alcohol in humans places requirements on the performance of the instrumentation due to the small size of the alcohol absorption spectrum relative to the water absorption of the body. In addition, interferences due to absorption of other spectroscopically active compounds such as collagen, lipids, protein, etc. reduce the useful portions of the alcohol absorption spectrum, yielding a net attribute signal that is small. To first order approximation, 1 mg/dl of alcohol concentration change is equivalent to 7 $\mu Au$ of spectral variance for the effective pathlength light travels through tissue in some embodiments of the present invention. Therefore, in order to measure alcohol non-invasively with clinically acceptable accuracy, the spectrometer portion of the non-invasive alcohol monitor must have sufficient signal-to-noise ratio (SNR) and sufficient photometric accuracy.

An FTIR spectrometer can achieve the required high SNR and photometric accuracy. In the art, there are many variants of the classic Michelson interferometer design depicted in FIG. 18. An example interferometer design is disclosed in U.S. patent application Ser. No. 09/415,600, filed Oct. 8, 1999, entitled "Interferometer Spectrometer with Reduced Alignment Sensitivity," the disclosure of which is incorporated herein by reference. Other example designs can be found in U.S. patent application Ser. Nos. 10/342,578 and 10/614,267. The FTIR spectrometer has throughput advantages (Jaquinot and Fellget advantages) relative to dispersive spectrometers and acousto-optical tunable filters. In addition to high throughput, the use of a reference laser in the FTIR spectrometer gives the device excellent wavelength axis precision. Wavenumber or wavelength axis precision can be important for effective calibration maintenance and calibration transfer.

The FTIR spectrometer subsystem 300 can provide thermal stability, spectral complexity and modulation efficiency performance in ranges that provide a suitably accurate measurement. In some applications of the present invention, ambient temperature and relative humidity can vary with time. Over an ambient temperature operating range of 10° C. to 35° C., the FTIR spectrometer can maintain a suitable modulation efficiency, for example 50% or better, to maintain a desirable level of performance. Modulation efficiency is a measure of the useful signal produced by the FTIR spectrometer and can be calculated by taking the ratio of the peak interferogram value at zero path difference to the DC value and then multiplying by 100. The maximum theoretical value of modulation efficiency is 100% with typical FTIR spectrometers achieving values in the range of 65% to 95%. FTIR spectrometers with modulation efficiencies below 50% have relatively poorer SNR because of the additional Shot noise from the larger proportion of non-signal bearing DC light falling on the photodetector.

In some embodiments, the FTIR spectrometer's change in percent transmittance (% T) at wavelengths between 1.2 and 2.5 microns (8000 to 4000 $cm^{-1}$) can be kept to no more than 1% per degree Celsius. This temperature sensitivity can preserve the alcohol net analyte SNR and simplify calibration maintenance.

The spectral shape changes induced by thermal drift of the FTIR spectrometer can be simple in shape such that they do not significantly degrade the net attribute signal. In one method used to quantify thermal drift for an FTIR subsystem, or the entire system, the device can be placed in a temperature controlled chamber and then spectra measured of a stable reference sample, such as an integrating sphere, as a function of time and temperature change in the chamber. A principle components analysis can be performed on the resulting absorbance spectra from the experiment and 99.99% of the variance due to thermal changes should be explained in the first 5 eigen vectors from the principle components analysis. In some embodiments, the % T change with temperature can be calculated from the data set, and the calculated temperature coefficient should be 1% per degree Celsius or less.

Examination of FIG. 1 shows two alternate configurations of the present invention. The primary difference is the location of the tissue sampling subsystem relative to the spectrometer subsystem. When the tissue sampling subsystem follows the spectrometer subsystem, several additional embodiments of the invention become apparent. In these embodiments, the spectrometer can be combined with the illumination subsystem such that only the wavelengths of interest are produced. In these embodiments, the combined illumination-spectrometer subsystem's fundamental building blocks are: one or more sources of specific wavelengths of light and some means to combine them. In one example embodiment there are multiple, individually addressed, sources (e.g. laser diodes, Vertical Cavity Emitting Laser (VCSEL), Quantum Dots, and/or Light Emitting Diodes (LEDs)) that illuminate the tissue directly. The tissue then serves as the means to combine the various wavelengths. In other embodiments, the light emitted by the individual sources is combined with a dedicated device such as an integrating chamber or a dispersive element (prism or grating). This device combines the multiple sources into a single output beam.

In the above embodiments, each source is modulated in time at a frequency that differs from the other sources in the subsystem. The modulation process is easily accomplished with semiconductor light sources that can be rapidly turned on and off at a variety of frequencies. The combined beam, that contains the various wavelengths that have been uniquely modulated, is equivalent in purpose to the beam that would be obtained from a single broadband source that is subsequently modulated or dispersed by a dedicated spectrometer subsystem. The combined beam is then introduced to the tissue sampling subsystem and ultimately the detector in the data acquisition subsystem. The data acquisition subsystem then decodes the signal into its individual wavelength components via a process similar to a Fourier or Hadamard transform.

A difficulty with these simplistic approaches is that the system does not sense any source wavelength drift, which can be problematic for the analysis routines. In an extreme case, one source (or wavelength channel) could drift in wavelength such that it overlaps the emission of another source leading to erroneous data. To prevent this from occurring, some wavelength "locking" function could be included. The locking mechanism could be incorporated with the spectral combining element, so that the sources are stable relative to each other. U.S. Pat. No. 6,529,543 outlines a method to accomplish this by utilizing a common end-mirror for all the lasers used in the system. Another approach would involve using a common Fabry-Perot etalon within all the laser cavities to force the emission to occur at fixed wavelengths imposed by the etalon. Yet another embodiment could utilize individually locked sources, for instance, a laser diode bar with distributed feedback gratings.

Data Acquisition Subsystem

Figure 20:
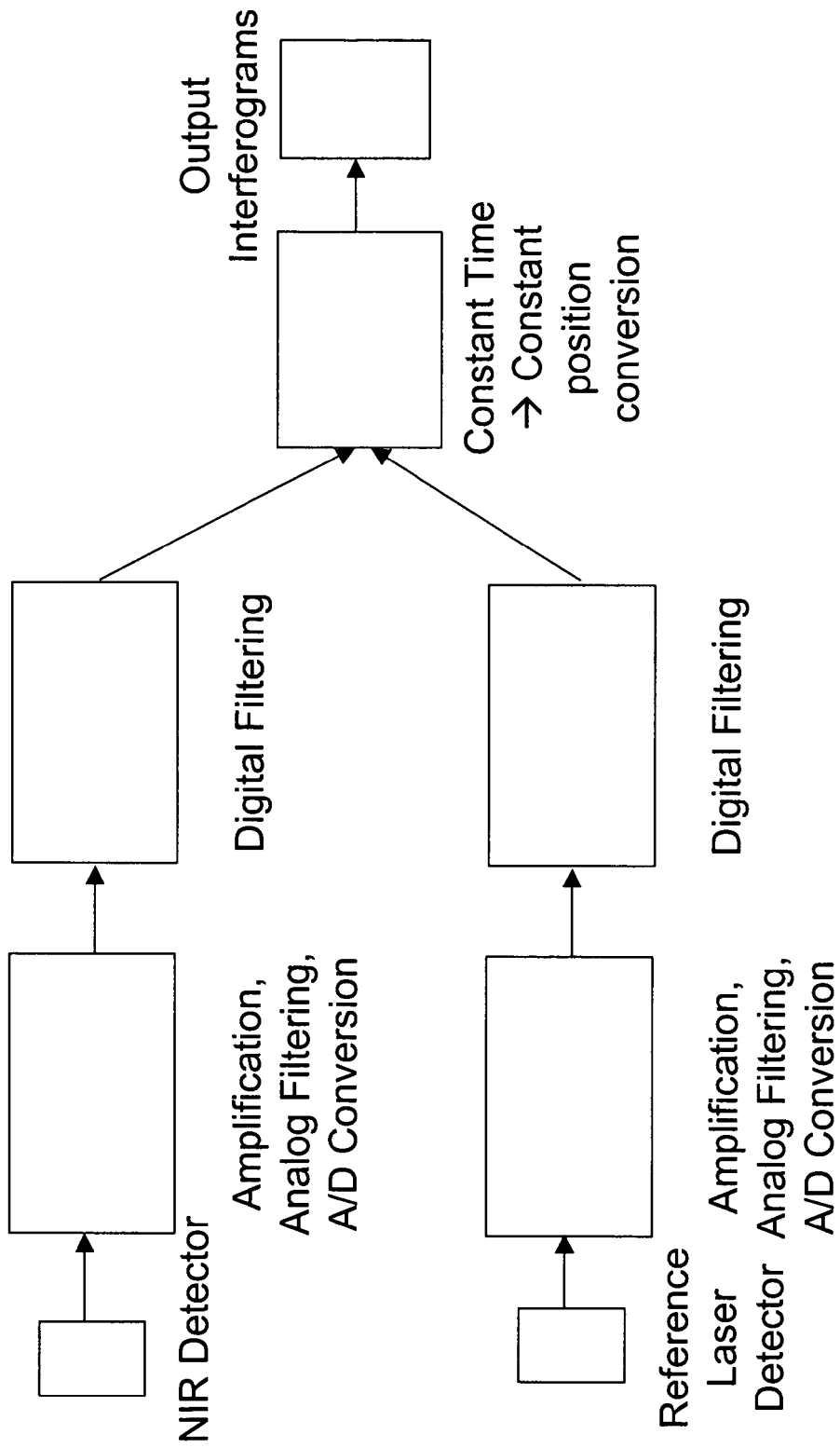
FIG. 20 is a schematic representation of the data acquisition subsystem.

Depending on the configuration of the system, the data acquisition subsystem 400 converts the optical signal from either the interferometer or sampling subsystem into interferograms that have been sampled at defined (e.g., equal) position intervals of the moving mirror of the interferometer. FIG. 20 is a schematic representation of the data acquisition subsystem. The detector begins this process by converting the input optical electrical to an electrical signal. Examples of detectors that are sensitive in the spectral range of 1.2 to 2.5 µm include InGaAs, InAs, InSb, Ge, PbS, and PbSe detectors. Some embodiments of the present invention can utilize a 1-mm, thermo-electrically cooled, extended range InGaAs detector that is sensitive to light in the 1.2 to 2.5 µm range. The 2.5 µm, extended range InGaAs detector has low Johnson noise and, as a result, allows Shot noise limited performance for the photon flux emanating from the illumination/tissue sampler/FTIR spectrometer subsystems. The extended InGaAs detector has peak sensitivity in the 2.0 to 2.5 µm spectral region where important alcohol absorption features are located. Unlike the liquid nitrogen cooled InSb detector, the thermo-electrically cooled, extended range InGaAs is practical for a commercial product. Also, this detector exhibits over 120 dbc of linearity in the 1.2 to 2.5 µm spectral region.

Any photodetector can be used with the present invention as long as the given photodetector satisfies basic sensitivity, noise and speed requirements. A suitable photodetector can have a shunt resistance greater than 6000 ohms, a terminal capacitance less than 6 nano farads and a minimum photosensitivity of 0.15 amps per watt over the 1.2 to 2.5 micron spectral region. In addition, the photodetector can have a cut-off frequency greater than or equal to 1000 hertz. The shunt resistance of the photodetector defines the Johnson or thermal noise of the detector. The Johnson noise of the detector must be low relative to the photon flux at the detector to ensure Shot noise limited performance by the detector. The terminal capacitance governs the cut-off frequency of the photodetector and can also be a factor in the high frequency noise gain of the photodetector amplifier. The photosensitivity can be an important factor in the conversion of light to an electrical current and can directly impact the signal portion of the SNR equation.

The remainder of the data acquisition subsystem 400 amplifies and filters the electrical signal from the detector and can convert the resulting analog electrical signal to its digital representation with an analog to digital converter, digital filtering, and re-sampling of the digital signal from equal time spacing to equal position spacing. The analog electronics and ADC can support the high SNR and linearity inherent in the interferogram. A data acquisition subsystem 400 that support at least 100 dbc of SNR plus distortion can preserve the SNR and linearity of the interferogram. The data acquisition subsystem 400 can produce a digitized interferogram that has uniform spatial displacement between samples. The data acquisition subsystem 500 also receives the reference laser signal from the FTIR spectrometer subsystem 300. In some embodiments, both the NIR signal and the reference laser can be digitized by a 24-bit delta-sigma ADC operated at 96 kilohertz. The digital output of the ADC can be processed by a signal processor to produce an interferogram that is sampled at constant spatial intervals. The interferograms can be passed to an embedded computer subsystem 600 for further processing, as discussed below. Traditionally, the zero crossings of a reference laser are utilized to mark constant spatial intervals for sampling of the interferogram. The zero crossings of a reference laser are spaced at intervals equal to half the wavelength of the monochromatic light emitted by the laser.

Further, the data acquisition subsystem 400 can utilize a constant time sampling, dual channel, delta-sigma analog-to-digital converter (ADC) to support the SNR and photometric accuracy requirements of the desired non-invasive measurement. In some embodiments, the delta-sigma ADC utilized supports sampling rates of over 100 kHz per channel, has a dynamic range in excess of 117 dbc and has total harmonic distortion less than −105 dbc.

There are other types of data acquisition systems for the FTIR spectrometer and photodetector that are well known in the art and can be employed in the present invention if they provide suitable performance characteristics for constant spatial sampling, dynamic range, SNR, harmonic distortion and sampling speed. The spatial sampling interval determination can have a maximum spatial sampling jitter of +/−25 nanometers in order to preserve a SNR of 100 dbc at 1.2 microns (8000 cm$^{-1}$). Levels of spatial sampling jitter greater than +/−25 nanometers can introduce frequency modulation artifacts into the spectral and degrade the alcohol net attribute signal. In addition, the data acquisition subsystem can support a dynamic range of at least 100 dbc, a SNR of 90 dbc and have total harmonic distortion less than 90 dbc. Finally, the ADC of the data acquisition subsystem can be able to sample at speeds of 5,000 samples per second or greater to support a minimum FTIR moving mirror scanning speed of 0.25 centimeters per second.

The constant time sampling data acquisition subsystem 400 has several distinct advantages over other methods of acquiring interferograms from an FTIR spectrometer. These advantages include greater dynamic range, lower noise, reduced spectral artifacts, detector noise limited operation and simpler and less expensive analog electronics. In addition, the constant time sampling technique improves the vibration immunity of the FTIR because it can digitally compensate for delay mismatches between the laser reference and infrared detectors and can back out the non-ideal aspects of the electronics' transfer function. The constant time sampling technique can require increased computational and memory resources to translate the constant time samples of the interferogram to constant spatial samples. With the use of a high performance digital signal processor (DSP), the additional computation and memory requirements can be outweighed by the performance enhancements of the constant time sampling technique.

Computing Subsystem

Figure 21:
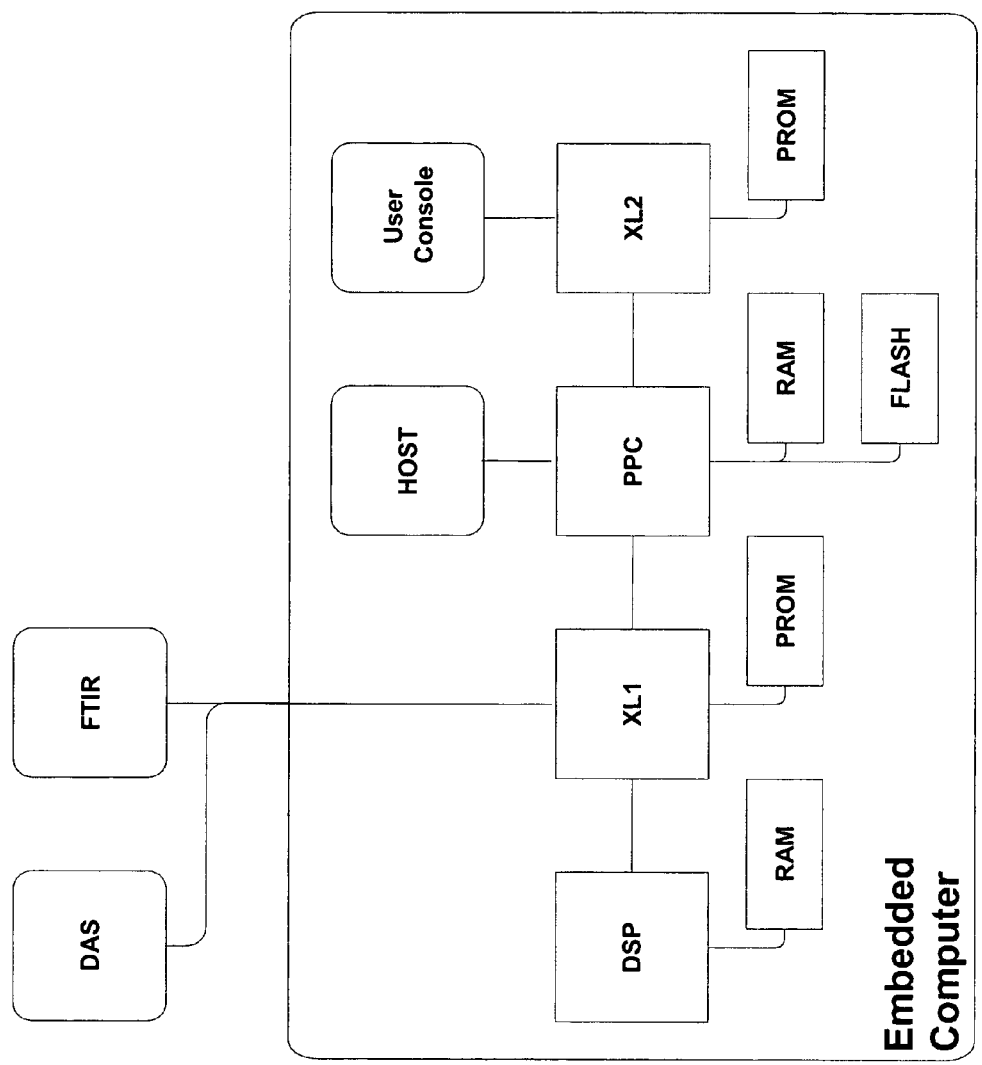
FIG. 21 is a schematic representation that shows the various aspects of the computing subsystem.

The computing subsystem 500 can perform multiple functions such as converting the digital interferograms obtained from the data acquisition subsystem 400 to single beam spectra, performing spectral outlier checks on the single beam spectra, spectral preprocessing in preparation for prediction of the attribute of interest, prediction of the attribute of interest, system status checks, all display and processing requirements associated with the user interface, and data transfer and storage. FIG. 21 is a schematic representation that shows the various aspects of the computing subsystem. In some embodiments, the computing subsystem comprises a dedicated personal computer or laptop computer that is connected to the other subsystems of the invention. In other embodiments, the computing subsystem comprises a dedicated, embedded computer.

The computing subsystem 500 can convert each digitized, constant spatially sampled interferogram from the data acquisition subsystem to a single beam spectrum by windowing the interferogram, performing phase correction of the windowed interferogram and then taking the Fourier transform of the windowed and phase corrected interferogram. Example windows include the boxcar, Gaussian, Blackman, and Tukey functions. Mertz, Forman, and power phase correction methods can be used. The power phase correction method can be simpler to implement, but can result in noise that has non-zero mean and is larger in magnitude by a factor of 1.414. The Mertz and Forman phase correction methods can be more complicated but can produce noise with zero mean and not inject noise from the imaginary portion of the complex spectrum. The Mertz and Forman methods can result in spectra with higher photometric accuracy. However, when using multivariate analysis techniques, all three phase correction methods can result in acceptable prediction performance.

After converting the interferograms to single beam spectra, the computer system can preferably check the single beam spectra for outliers or bad scans. An outlier sample or bad scan is one that violates the hypothesized relationship between the measured signal and the properties of interest. Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. The calibration model is discussed in connection with the calibration subsystem elsewhere herein. Any outliers or bad scans can be deleted and the remaining good spectra can be averaged together to produce an average single beam spectrum for the measurement. The average single beam spectrum can be converted to absorbance by taking the negative base 10 logarithm (log 10) of the spectrum. The absorbance spectrum can be scaled by a single beam spectrum to renormalize the noise.

The scaled absorbance spectrum can be used to determine the attribute of interest in conjunction with the calibration model that is obtained from the calibration subsystem 600. After determination of the attribute of interest, the computing subsystem 500 can report the result 830 to the subject. The computing subsystem 500 can also report the level of confidence in the goodness of the result. If the confidence level is low, the computing subsystem 500 can withhold the result and ask the subject to retest. If required, additional information can be conveyed that directs the user to perform a corrective action. See, e.g. U.S. patent application Ser. No. 10/410,006, "Reduction of Errors in Non-Invasive Tissue Sampling," incorporated herein by reference. The results can be reported visually on a display, by audio and/or by printed means. Additionally, the results can be stored to form a historical record of the attribute. In other embodiments, the results can be transferred to a remote monitoring or storage facility via the internet, phone line, or cell phone service.

The computing subsystem 500 includes a central processing unit (CPU), memory, storage, a display and preferably a communication link. An example of a CPU is the Intel Pentium microprocessor. The memory can be, e.g., static random access memory (RAM) and/or dynamic random access memory. The storage can be accomplished with non-volatile RAM or a disk drive. A liquid crystal display can be suitable. The communication link can be, as examples, a high speed serial link, an Ethernet link, or a wireless communication link. The computer subsystem can, for example, produce attribute measurements from the received and processed interferograms, perform calibration maintenance, perform calibration transfer, run instrument diagnostics, store a history of measured alcohol concentrations and other pertinent information, and in some embodiments, communicate with remote hosts to send and receive data and new software updates.

The computing system 500 can also contain a communication link that allows transfer of a subject's alcohol measurement records and the corresponding spectra to an external database. In addition, the communication link can be used to download new software to the computer and update the multivariate calibration model. The computer system can be viewed as an information appliance. Examples of information appliances include personal digital assistants, web-enabled cellular phones and handheld computers.

Calibration Subsystem

A calibration model can be used to obtain alcohol measurements. In some embodiments, the calibration model is formed by acquiring reference measurements and contemporaneous spectroscopic data on multiple subjects in a wide variety of environmental conditions. In these embodiments, spectroscopic data can be acquired from each subject over a range of alcohol concentrations. In other embodiments, a hybrid calibration model can be to measure the alcohol concentrations of subject spectra. In this case, the term hybrid model denotes that a partial least squares (PLS) calibration model was developed using a combination of in vitro and in vivo spectral data. The in vitro portion of the data can comprise a 0.1 mm pathlength transmission spectrum of 500 mg/dL alcohol in water measured using the non-invasive measurement system configured for transmission measurements. The transmission spectrum can be ratioed to a 0.1 mm pathlength transmission spectrum of water, converted to absorbance, and normalized to unit pathlength and concentration.

Figure 22:
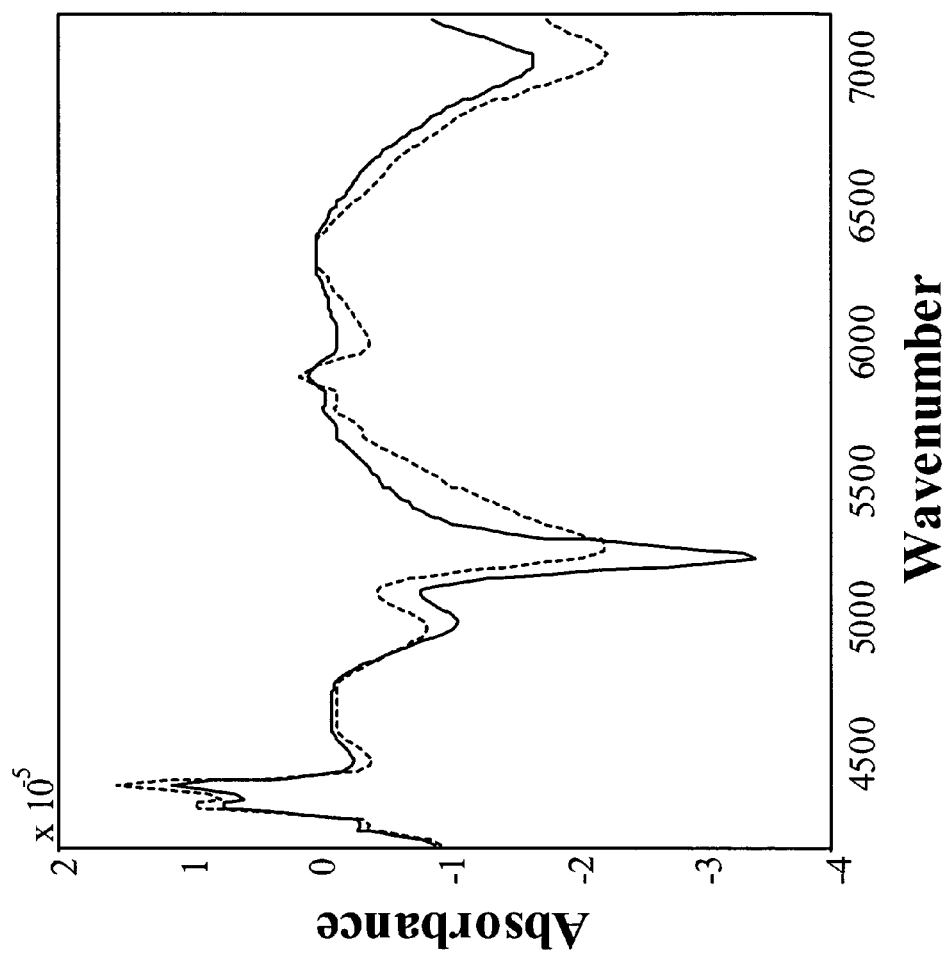
FIG. 22 is the spectrum of water before and after path length correction to account for photon propagation through tissue.

Light propagation through tissue is a complex function of the diffuse reflectance optical tissue sampler design, physiological variables, and wavenumber. Consequently, the pathlength of light through tissue has a wavenumber dependence that is not encountered in scatter-free transmission measurements. In order to account for the wavenumber dependence, the interaction of the optical tissue sampler with the scattering properties of human tissue can be modeled via Monte-Carlo simulation using a commercial optical ray-tracing software package (TracePro). Using the resulting model of the photon-tissue interactions, an estimate of the effective pathlength of light through the dermis and subcutaneous tissue layers as a function of wavenumber was generated. The effective pathlength ($l_{eff}$) is defined as $$l_{eff}(v) = \frac{\sum_{i=1}^{N} l_i \exp(-\mu_a(v) l_i)}{\sum_{i=1}^{N} l_i},$$

where $v$ is wavenumber, $l_i$ is the pathlength traversed by the $i^{th}$ ray in the Monte Carlo simulation [mm], N is the total number of rays in the simulation, and $\mu_a$ is the (wavenumber-dependent) absorption coefficient [mm$^{-1}$]. Due to its large absorption in vivo, water is the only analyte that has a significant effect on the effective pathlength. Therefore, for the purposes of the effective pathlength calculation, the absorption coefficients used were those of water at physiological concentrations. The alcohol absorbance spectrum (as measured in transmission) was then scaled by the computed path function to form a corrected alcohol spectrum representative of the wavenumber dependent pathlength measured by the diffuse reflectance optical sampler. FIG. 22 shows the alcohol absorbance spectrum before and after correction by the path function. This corrected spectrum formed the base spectrum for the mathematical addition of alcohol to the calibration spectra.

Figure 23:
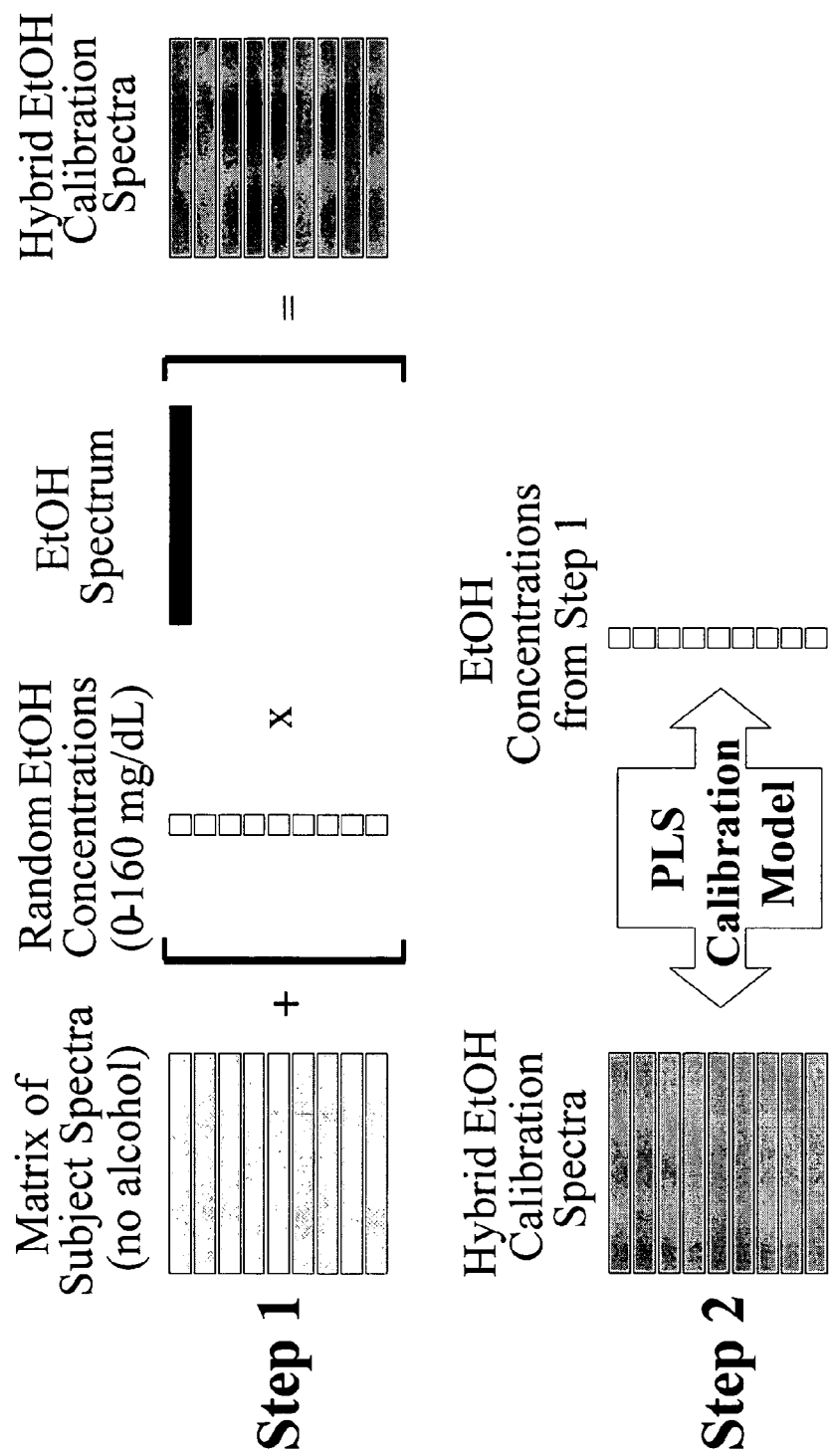
FIG. 23 is a diagram of the hybrid calibration formation process.

The in vivo data comprised noninvasive tissue spectra collected from persons who had not consumed alcohol. A hybrid model was formed by adding the alcohol pure component spectrum, weighted by various alcohol "concentrations" (ranging from 0 to 160 mg/dL), to the noninvasive tissue spectral data. The PLS calibration model was built by regressing the synthetic alcohol concentrations on the hybrid spectral data. FIG. 23 is a schematic representation of the hybrid calibration formation process. The hybrid calibration in this work used approximately 1500 non-invasive tissue spectra that were collected from 133 subjects over three months.

The use of hybrid calibration models, rather than calibration models built from spectra acquired from subjects who have consumed alcohol, can provide advantages. The hybrid modeling process makes it possible to generate calibration spectra that contain higher concentrations (up to 160 mg/dL in one example) of alcohol than would be considered safe for consumption in a human subject study (120 mg/dL is considered a safe upper limit). The result is a stronger calibration with a wider range of analyte concentrations that is able to predict higher alcohol concentrations more accurately. This can be important because alcohol concentrations observed in the field can be more than double the maximum safe dosage in a clinical research setting. The hybrid calibration process also allows the prevention of correlations between alcohol and the spectral interferants in tissue. For example, the random addition of alcohol signal to the calibration spectra prevents alcohol concentration from being correlated with water concentration. Thus, the hybrid approach reduces the possibility that the measurement could spuriously track changes in tissue water content instead of alcohol concentration.

Once formed, a calibration should remain stable and produce accurate attribute predictions over a desired period of time. This process is referred to as calibration maintenance and can comprise multiple methods that can be used individually or in conjunction. The first method is to create the calibration in a manner that inherently makes it robust. Several different types of instrumental and environmental variation can affect the prediction capability of a calibration model. It is possible and desirable to reduce the magnitude of the effect of instrumental and environmental variation by incorporating this variation into the calibration model.

It is difficult, however, to span the entire possible range of instrument states during the calibration period. System perturbations can result in the instrument being operated outside the space of the calibration model. Measurements made while the instrument is in an inadequately modeled state can exhibit prediction errors. In the case of in vivo optical measurements of medically significant attributes, these types of errors can result in erroneous measurements that degrade the utility of the system. Therefore it is often advantageous to use additional calibration maintenance techniques during the life of the instrument in order to continually verify and correct for the instrument's status.

Examples of problematic instrument and environmental variation include, but are not limited to: changes in the levels of environmental interferants such as water vapor or $CO_2$ gas, changes in the alignment of the instrument's optical components, fluctuations in the output power of the instrument's illumination system, and changes in the spatial and angular distribution of the light output by the instrument's illumination system.

Calibration maintenance techniques are discussed in commonly assigned U.S. patent application Ser. No. 09/832,608, "Optically Similar Reference Samples and Related Methods for Multivariate Calibration Models Used in Optical Spectroscopy," and U.S. patent application Ser. No. 10/281,576, "Optically Similar Reference Samples," and U.S. patent application Ser. No. 10/733,195, "Adaptive Compnesation for Measurement Distortions in Spectroscopy," each of which is incorporated herein by reference. These methods use an environmentally inert non-tissue sample, such as an integrating sphere, that optionally contains the attribute of interest, in order to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predicable over time. Any unexplained change in the spectra acquired from the sample over time indicate that the instrument has undergone a perturbation or drift due to environmental effects. The spectral change can then be used to correct subsequent tissue measurements in humans in order to ensure and accurate attribute measurement.

Once a calibration is formed, it is desirable to transfer the calibration to existing and future instruments. This process is commonly referred to as calibration transfer. While not required, calibration transfer prevents the need for a calibration to be built on each system that is manufactured. This represents a significant time and cost savings that could result in the difference between success or failure of a commercial product. Calibration transfer arises from the fact that optical and electronic components vary from unit to unit which, in aggregate, results in a significant difference in spectra obtained from multiple instruments. For example, two light sources could have different color temperatures thereby resulting in a different light distribution for the two sources. The responsivity of two detectors can also differ significantly, which can result in additional spectral differences.

Similar to calibration maintenance, multiple methods can be used in order to effectively achieve calibration transfer. The first method is to build the calibration with multiple instruments. The presence of multiple instruments allows the spectral variation associated with instrument differences to be determined and made orthogonal to the attribute signal during the calibration formation process. While this does approach reduces the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. The samples described in the calibration maintenance section are also applicable to calibration transfer. See, e.g. U.S. Pat. No. 6,441,388, incorporated herein by reference.

Additional Aspects of the Present Invention

Calibration Check Samples

In addition to helping to ensure subject safety, disposable calibration check samples can be used to verify that the instrument is in proper working condition. In many commercial applications of alcohol measurements, the status of the instrument must be verified to ensure that subsequent measurements will provide accurate alcohol concentrations or attribute estimates. The instrument status is often checked immediately prior to a subject measurement. In some embodiments, the calibration check sample can include alcohol. In other embodiments, the check sample can be an environmentally stable and spectrally inert sample, such as an integrating sphere. The check sample can be a gas or liquid that is injected or flowed through a spectroscopic sampling chamber. The check sample can also be a material, such as a gel, that can contain alcohol. The check sample can be constructed to interface with the sampling subsystem or can be incorporated into another area of the optical path of the system. These examples are meant to be illustrative and are not limiting to the various possible calibration check samples.

Direction of Change (DOC) and Rate of Change (ROC)

The present invention also comprises a method for measurement of the direction and magnitude of concentration changes of tissue constituents, such as alcohol, using spectroscopy. The non-invasive measurement obtained from the current invention is inherently semi-time resolved. This allows attributes, such as alcohol concentration, to be determined as a function of time. The time resolved alcohol concentrations can then be used to determine the rate and direction of change of the alcohol concentration. In addition, the direction of change information can be used to partially compensate for any difference in blood and non-invasive alcohol concentration that is caused by physiological kinetics. See, e.g., U.S. patent application Ser. No. 10/753,506, "Noninvasive determination of direction and rate of change of an analyte," incorporated herein by reference. A variety of techniques for enhancing the rate and direction signal have been uncovered. Some of these techniques include heating elements, rubrifractants, and index-matching media. They should not be interpreted as limiting the present invention to these particular forms of enhancement or equilibration. These enhancements are not required to practice the present invention, but are included for illustrative purposes only.

Subject Safety

Another aspect of non-invasive alcohol measurements is the safety of the subjects during the measurements. In order to prevent measurement contamination or transfer of pathogens between subjects it is desirable, but not necessary, to use disposable cleaning agents and/or protective surfaces in order to protect each subject and prevent fluid or pathogen transfer between subjects. For example, in some embodiments an isopropyl wipe can be used to clean each subject's sampling site and/or the sampling subsystem surface prior to measurement. In other embodiments, a disposable thin film of material such as ACLAR can be placed between the sampling subsystem and the subject prior to each measurement in order to prevent physical contact between the subject and the instrument. In other embodiments, both cleaning and a film can be used simultaneously. As mentioned in the sampling subsystem portion of this disclosure, the film can also be attached to a positioning device and then applied to the subject's sampling site. In this embodiment, the positioning device would interface with the sampling subsystem and prevent the subject from moving during the measurement while the film serves its protective role.

Topical Interferants

Figure 24:
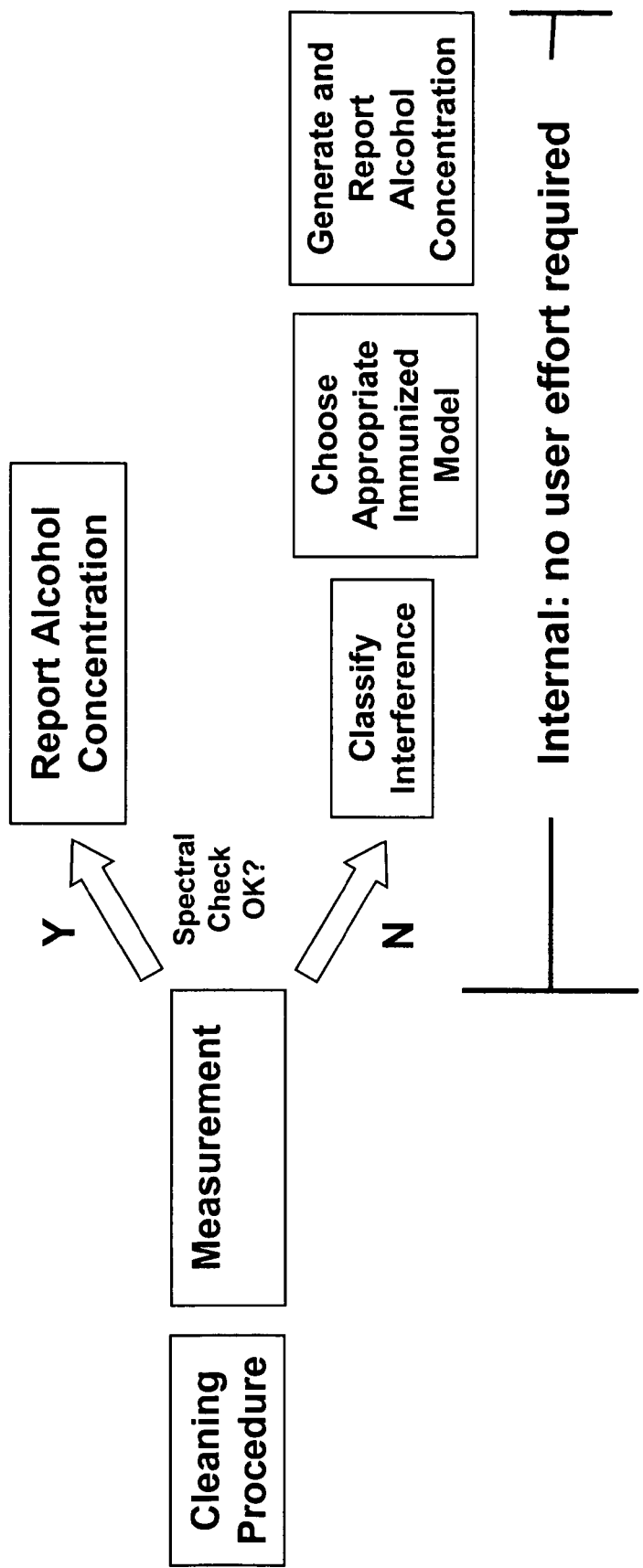
FIG. 24 is a schematic representation of a decision process that combines three topical interferant mitigation strategies.

In subject measurements the presence of topical interferants on the sampling site can be a significant concern. Many topical interferants have spectral signatures in the near infrared region and can therefore contribute significant measurement error when present. The present invention contemplates at least three methods, that can be used individually or in combination, for accommodating the potential for topical interferants. FIG. 24 shows a flow diagram that describes a method for combining the three topical interferant mitigation approaches into one combined process. First, a disposable cleaning agent similar to that described in the subject safety section can be used. The use of the cleaning agent can either be at the discretion of the system operator or a mandatory step in the measurement process. Multiple cleaning agents can also be used that individually target different types of topical interferants. For example, one cleaning agent can be used to remove grease and oils, while another can be used to remove consumer goods such as cologne or perfume. The cleaning agents remove topical interferants prior to the attribute measurement in order to reduce their effect on the accuracy of the system.

Figure 25:
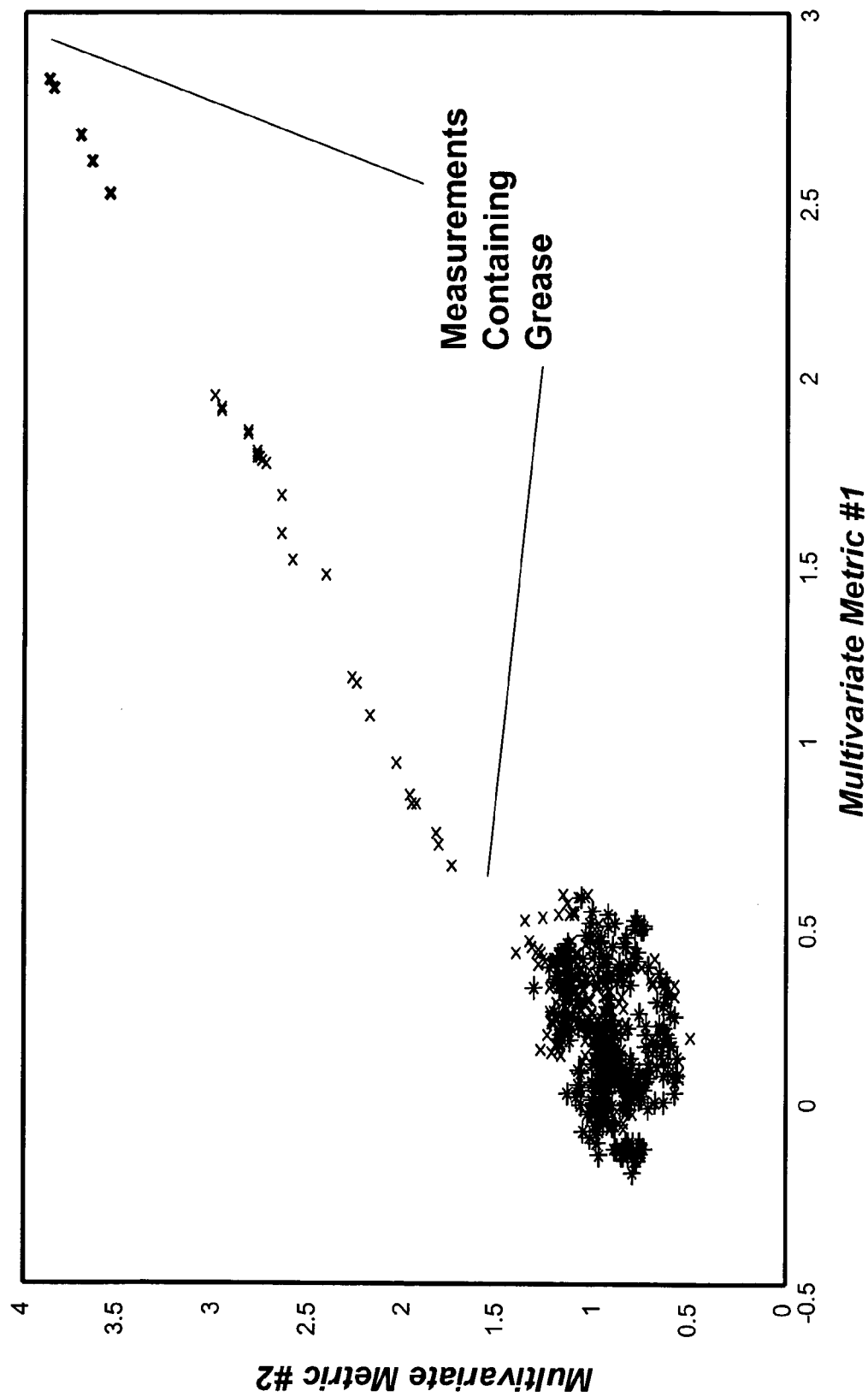
FIG. 25 demonstrates the effectiveness of multivariate calibration outlier metrics for detecting the presence of topical interferants.

The second method for mitigating the presence of topical interferants is to determine if one or more interferants is present on the sampling site. The multivariate calibration models used in the calibration subsystem offer inherent outlier metrics that yield important information regarding the presence of un-modeled interferants (topical or otherwise). As a result, they provide insight into the trustworthiness of the attribute measurement. FIG. 25 shows example outlier metric values from noninvasive measurements using the present invention acquired during the clinical studies. All of the large metric values (clearly separated from the majority of the points) correspond to measurements where grease had been intentionally applied to the subject's sampling site. These metrics do not specifically identify the cause of the outlier, but they do indicate that the associated attribute measurement is suspect. An inflated outlier metric value (a value beyond a fixed threshold, for example) can be used to trigger a fixed response such as a repeat of the measurement, application of an alternative calibration model, or a sampling site cleaning procedure. This is represented in FIG. 24 as the "Spectral Check OK" decision point.

The final topical interferant mitigation method adapts the calibration model to include the spectral signature of the topical interferant. The adapted calibration model can either be created on demand or selected from an existing library of calibration models. Each calibration in the library can be targeted at mitigating a different interferant or class of interferants such as oils. In some embodiments, the appropriate calibration model can be chosen based on the portion of an acquired spectrum that is unexplained by the original calibration model. This portion of the spectrum is referred to as the calibration model residual. Because each topical interferant or class of interferants has a unique near infrared spectrum, the calibration model residual can be used to identify the topical interferant.

The model residual or the pure spectrum (obtained from a stored library) of the interferants can then be incorporated into the spectra used to form the calibration. The multivariate calibration is then reformed with the new spectra such that the portion of the attribute signal that is orthogonal to the interferant can be determined. The new calibration model is then used to measure the attribute of interest and thereby reduce the effects of the topical interferant on attribute measurement accuracy. The resulting model will reduce the effect of the interferant on the alcohol measurement at the possible expense of measurement precision when no interferants are present. This process is referred to as calibration immunization. The immunization process is similar to the hybrid calibration formation process shown in FIG. 23, but includes the additional step of the mathematical addition of the interferant's spectral variation. It should be noted that, due to the impact of the immunization process on measurement precision, it can be desirable to identify possible interferants for each measurement and immunize specifically against them rather than attempt to develop a calibration that is immunized against all possible interferants.

EXAMPLE RESULTS

Figure 26:
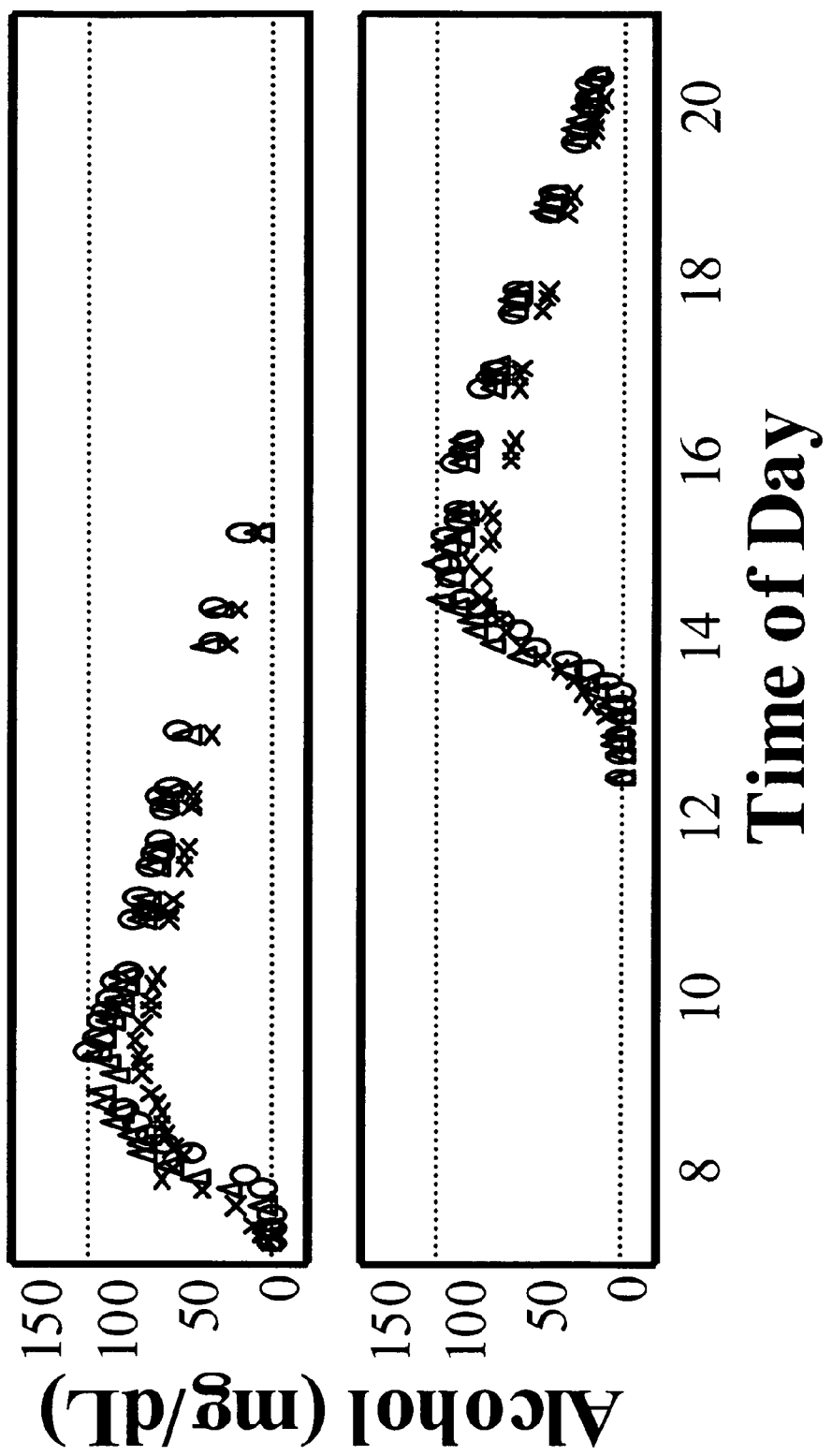
FIG. 26 shows blood, breath, and non-invasive alcohol (obtained from the present invention) over time for two subjects during induced alcohol excursions.
Figure 27:
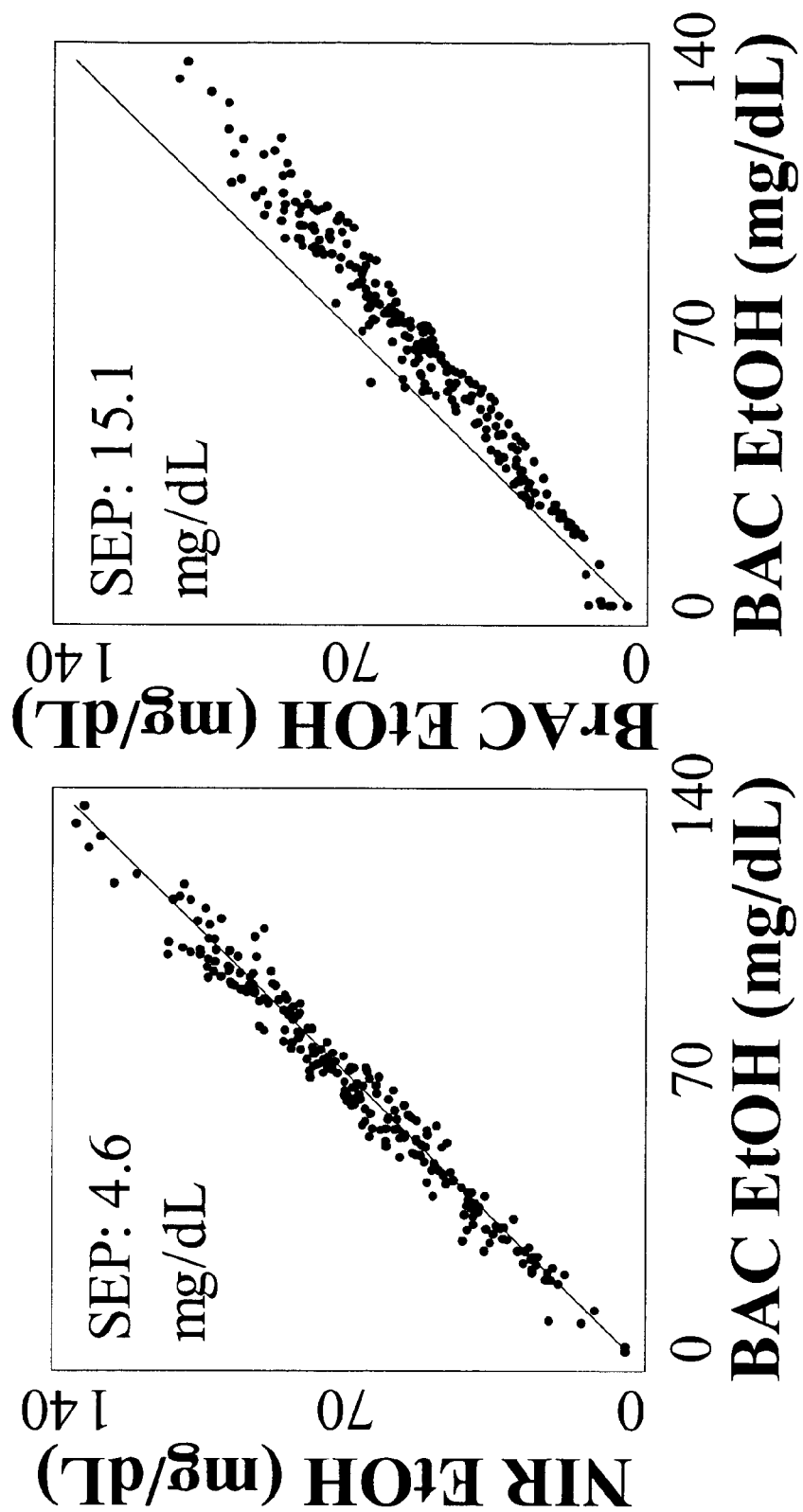
FIG. 27 is a graph of non-invasive alcohol measurements versus blood alcohol reference for multiple human subjects that demonstrates the ability of the system of the present invention to derive clinically relevant alcohol measurements.

FIG. 26 depicts the alcohol measurements acquired from an embodiment of the measurement system for two subjects during induced alcohol excursions. Each window contains the blood, breath, and noninvasive alcohol concentrations versus time that were measured during the alcohol excursion for that subject. FIG. 27 shows a side-by-side comparison of the current inventions (NIR) measurements versus blood (BAC) alcohol and breath (BrAC) versus blood (BAC) alcohol. FIG. 27 demonstrates that the breath measurements exhibit a proportional error relative to blood alcohol. This is due to the globally applied blood-breath partition coefficient of 2100 mg EtOH/dL blood per mg EtOH/dL air that relates the concentration of alcohol in expired air from the lungs to blood alcohol. The comparison of the breath and non-invasive measurements demonstrates that under identical experimental conditions the precision of the current invention's measurement is substantially equal to that of a commonly used state-of-the-art breath alcohol instrument. In addition, the non-invasive measurement accuracy is superior to the breath measurement because it does not exhibit a proportional error.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What we claim is:

1. An apparatus for non-invasive determination of an attribute of human tissue by quantitative near infrared spectroscopy comprising:
    an illumination subsystem;
    a tissue sampling subsystem, in optical communication with the illumination subsystem;

a spectrometer subsystem in optical communication with the tissue sampling subsystem, said spectrometer subsystem including a spectrometer;

a data acquisition subsystem including a detector which receives an output from the spectrometer subsystem and converts said output to a communicable representation, said data acquisition subsystem including means for modifying said communicable representation and producing an analyzable representation thereof; and a processing subsystem for receiving said analyzable representation and further including means for determining the attribute from said analyzable representation;

wherein the illumination subsystem comprises a source of light that is substantially spatially homogeneous and substantially angularly homogeneous.

2. An apparatus according to claim 1, wherein the illumination subsystem comprises a light homogenizer.

3. An apparatus according to claim 2, wherein the light homogenizer comprises a light pipe, wherein the light pipe has a polygonal cross-section along a portion of its length, and wherein the light pipe has an axis along the direction of light travel therethrough, and wherein the axis describes a bend.

4. An apparatus according to claim 2, wherein the light homogenizer comprises a light pipe having a diffuse internal surface.

5. An apparatus according to claim 2, wherein the light homogenizer comprises a glass diffuser.

6. An apparatus according to claim 2, wherein the illumination subsystem comprises a filament light source.

7. An apparatus according to claim 6, wherein the filament light source comprises a resistive element.

8. An apparatus according to claim 1, wherein the illumination subsystem comprises a source of light, and a chamber mounted with the source such that light from the source is collected by the chamber and directed to an output of the chamber, wherein the light source mounts with the chamber such that there is no direct optical path from the light source to the output.

9. An apparatus according to claim 1, wherein the tissue sampling subsystem comprises a first optical waveguide in optical communication with the illumination subsystem and adapted to communicate light to tissue, and a second optical waveguide in optical communication with the spectrometer and adapted to receive light from tissue.

10. An apparatus according to claim 1, wherein the illumination subsystem and tissue sampling subsystem comprise a light source, a chamber mounted with the light source such that light from the source is collected by the chamber and directed to an output of the chamber, wherein the light source mounts with the chamber such that there is no direct optical path from the light source to the output, a first optical waveguide in optical communication with the output of the chamber and adapted to communicate light to tissue, and a second optical waveguide in optical communication with the spectrometer subsystem and adapted to receive light from tissue.

11. An apparatus according to claim 10, wherein the chamber comprises a reflective internal surface, and wherein a portion of the internal surface is diffusively reflective.

12. An apparatus according to claim 1, wherein the tissue sampling subsystem comprises three rows of optical fibers, with two outer rows mounted on either side of an inner row, and wherein the outer rows are in optical communication with the illumination subsystem, and wherein the inner row is in optical communication with the spectrometer subsystem.

13. An apparatus according to claim 12, wherein the edges of fibers in adjacent rows are not less than 75 microns apart.

14. An apparatus according to claim 1, wherein the tissue sampling subsystem comprises a plurality of illumination fibers in optical communication with the illumination subsystem, and a plurality of detection fibers in optical communication with the spectrometer subsystem, wherein the illumination fibers are disposed at an angle to the detection fibers.

15. An apparatus according to claim 14, wherein the illumination fibers are disposed at an angle between 20 degrees and 30 degrees from normal to the tissue surface, inclined toward the detection fibers, and wherein the detection fibers are disposed at an angle between 20 degrees and 30 degrees from normal to the tissue surface, inclined toward the illumination fibers, and wherein each illumination fiber is separated from the nearest detection fiber inclined toward the illumination fiber by at least 75 microns.

16. The apparatus of claim 1, wherein the spectrometer subsystem comprises a VCSEL.

17. The apparatus of claim 1, wherein the processing subsystem comprises a multivariate model relating spectroscopic information to tissue attribute.

18. The apparatus of claim 17, wherein the multivariate model comprises in vivo tissue spectra and corresponding attribute values, and in vitro spectra and corresponding attribute values.

19. The apparatus of claim 17, wherein the multivariate model comprises in vivo tissue spectra and corresponding attribute values, and spectral information from interferants.

20. The apparatus of claim 1, wherein the tissue sampling subsystem comprises a positioning device mounted with the tissue of the subject.

21. The apparatus of claim 1, wherein the tissue sampling subsystem comprises an interface to tissue on a hand of a subject.

22. The apparatus of claim 1, wherein the tissue sampling subsystem comprises an interface to tissue on a fingertip of a subject.

23. The apparatus of claim 1, wherein the tissue sampling subsystem comprises a bracket mounted with a base which references an elbow of a subject's arm disposed thereon.

24. The apparatus of claim 23, wherein the tissue sampling subsystem comprises an adjustable hand rest spaced longitudinally from the bracket along the base.

25. An apparatus according to claim 1, wherein the tissue sampling subsystem comprises a plurality of optical fibers having a numerical aperture of about 0.22.

26. An apparatus for non-invasive determination of the presence, concentration, or both, of alcohol in human tissue by quantitative near infrared spectroscopy comprising:

an illumination subsystem, adapted to supply light having a plurality of wavelengths in the range of 1.2 microns to 2.5 microns;

a tissue sampling subsystem, in optical communication with the illumination subsystem, and adapted to emit light to a tissue surface and to collect light from the same tissue surface;

an interferometric spectrometer subsystem in optical communication with the tissue sampling subsystem, said interferometric spectrometer subsystem including an interferometer;

a data acquisition subsystem including a detector which receives an output from the spectrometer subsystem and converts said output to a representation suitable for communication and analysis; and a processing subsystem adapted to receive said representation and to determine the presence, concentration, or both, of alcohol from said representation by quantitative near infrared spectroscopic analysis;

wherein the processing subsystem comprises a multivariate model relating spectroscopic information to tissue attribute, and wherein the multivariate model uses information at more than three wavelengths, and wherein the tissue attribute comprises at least one of: the rate of change of alcohol concentration and the direction of change of alcohol concentration.

27. An apparatus for non-invasive determination of the presence, concentration, or both, of alcohol or a derivative thereof in human tissue by quantitative near infrared spectroscopy comprising:

an illumination subsystem, adapted to supply light having a plurality of wavelengths in the range of 1.2 microns to 2.5 microns wherein the illumination subsystem comprises a source of light that is substantially spatially homogeneous and substantially angularly homogeneous;

a spectrometer subsystem in optical communication with the illumination subsystem, said spectrometer subsystem including an interferometer;

a tissue sampling subsystem, in optical communication with the spectrometer subsystem, and adapted to emit light to a tissue surface and to collect light from the same tissue surface;

a data acquisition subsystem including a detector which receives an output from the tissue sampling subsystem and converts said output to a representation suitable for communication and analysis; and a processing subsystem for receiving said representation and for determining the attribute from said representation by quantitative near infrared spectroscopic analysis.

28. An apparatus according to claim 27, wherein the tissue sampling subsystem comprises a light homogenizer mounted such that light from the spectrometer subsystem is homogenized.

* * * * *